(12) United States Patent
Mulier et al.

(10) Patent No.: US 8,545,492 B2
(45) Date of Patent: Oct. 1, 2013

(54) DEVICE AND METHOD FOR RADIO FREQUENCY ABLATION (RFA)

(75) Inventors: Stefaan Michiel Maria Mulier, Leuven (BE); Gery Verhaegen, Rotselaar (BE); Michiel Willem Jozef Mulier, Boutersem (BE); Johan Lionel Van Den Bossche, Linden (BE); Kristoffel Pieter Maria Mulier, Hoegaarden (BE)

(73) Assignee: Vesalius Medical Technologies BVBA (BE)

( * ) Notice: Subject to any disclaimer, the term of this patent is extended or adjusted under 35 U.S.C. 154(b) by 0 days.

(21) Appl. No.: 13/636,077

(22) PCT Filed: Mar. 18, 2011

(86) PCT No.: PCT/EP2011/054160
§ 371 (c)(1),
(2), (4) Date: Feb. 6, 2013

(87) PCT Pub. No.: WO2011/113943
PCT Pub. Date: Sep. 22, 2011

(65) Prior Publication Data
US 2013/0012937 A1    Jan. 10, 2013

(30) Foreign Application Priority Data

Mar. 19, 2010 (EP) .................................... 10002922

(51) Int. Cl.
*A61B 18/18* (2006.01)
(52) U.S. Cl.
USPC .................................. 606/33; 606/41; 606/32

(58) Field of Classification Search
USPC ...................................................... 606/32–45
See application file for complete search history.

(56) References Cited

U.S. PATENT DOCUMENTS

2009/0036882 A1    2/2009   Webster et al.

FOREIGN PATENT DOCUMENTS

| EP | 1645239 A1 | 4/2006 |
| WO | 2004082498 A1 | 9/2004 |
| WO | 2005043324 A2 | 5/2005 |

OTHER PUBLICATIONS

EPO ISR, Jun. 29, 2011.
EPO IPRP, Jul. 11, 2012.

*Primary Examiner* — Linda Dvorak
*Assistant Examiner* — Amanda Scott
(74) *Attorney, Agent, or Firm* — Clifford D. Hyra; Symbus Law Group, LLC

(57) ABSTRACT

A device for radio frequency ablation (RFA) of diseased tissue has
  a mesh or plate with a grid of holes for holding electrodes;
  a plurality of electrodes with adaptable active tip length;
  means for visualizing and probing insertion depth of each of the electrodes in the diseased tissue;
  a switch box, connectable to the electrodes and adapted to distribute current between the electrodes during the RFA process;
  a control unit for controlling the switch box; and
  means for monitoring the RFA process.
The control unit is adapted to determine groups of electrodes, an electric mode for activation of each group of electrodes, a polarity for electrodes within each group of electrodes, an activation mode for the groups, a time interval and order for activation of the groups, a power output and current strength, and a duration of the RFA process.

22 Claims, 15 Drawing Sheets

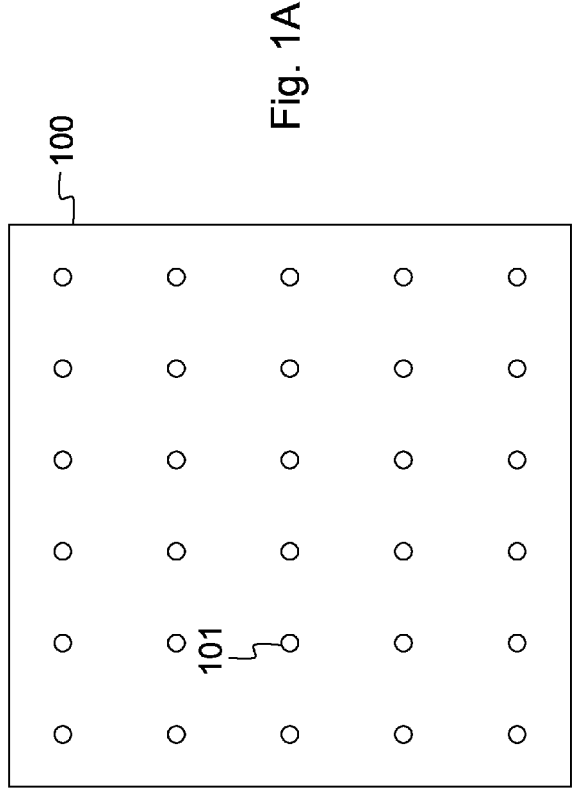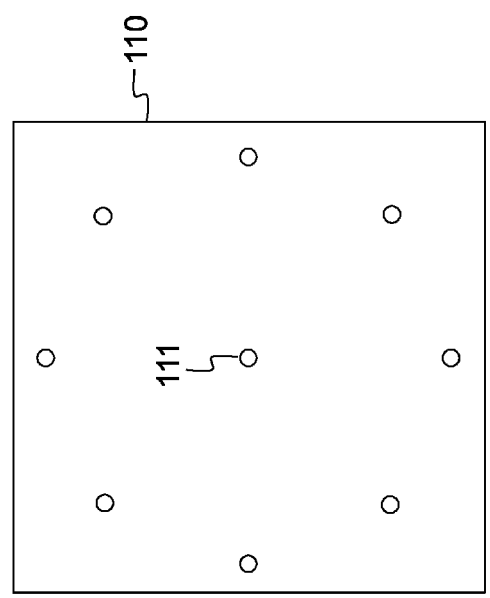

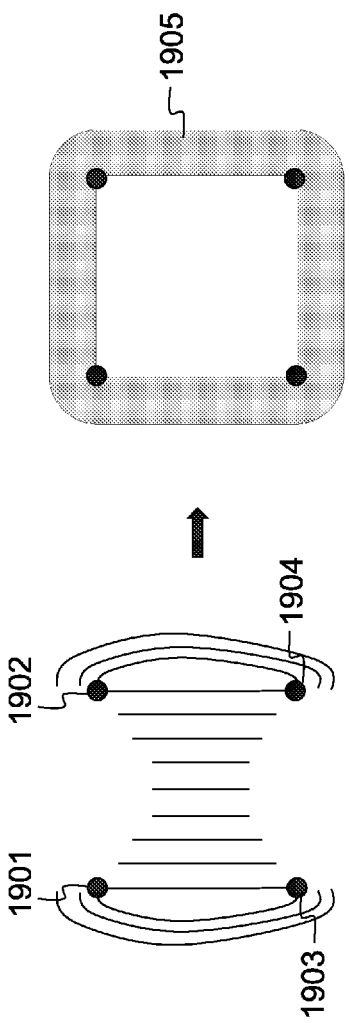
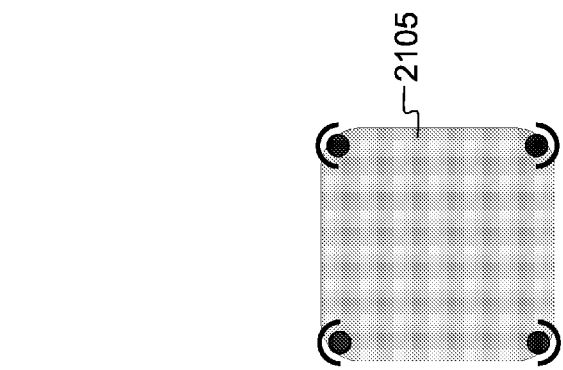
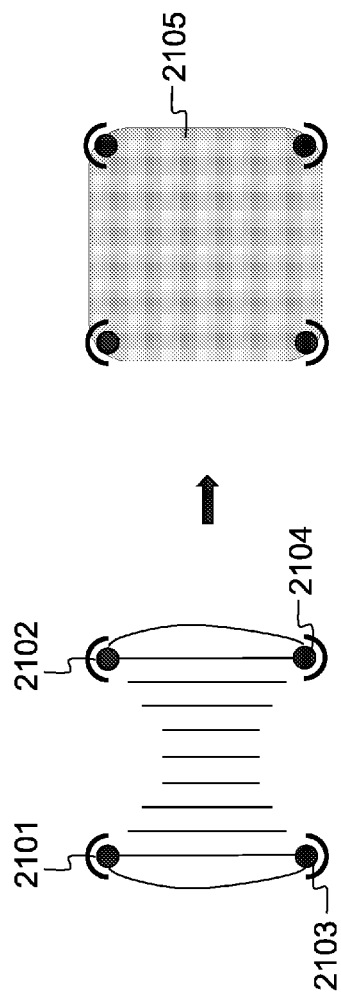

DEVICE AND METHOD FOR RADIO FREQUENCY ABLATION (RFA)

This application claims the benefit of European patent application No. 10002922.2, filed Mar. 19, 2010, which is hereby incorporated by reference in its entirety.

FIELD OF THE INVENTION

The present invention generally relates to radio frequency ablation or RFA, i.e. destruction of tissue in the form of coagulation necrosis caused primarily by resistive heating in the surrounding tissue and secondarily by passive heat conduction. The invention in particular concerns a device and method yielding reliable coagulation that is both predictable and adaptable to any size or shape of tumour or diseased tissue.

BACKGROUND OF THE INVENTION

Surgical resection is still considered as the primary option for the treatment of malignant tumours. For unresectable tumours, several interstitial techniques that achieve local tissue destruction have been developed, including radio frequency (RF) coagulation, cryosurgery, ethanol injection, interstitial laser therapy and microwaves. Among these techniques, RF coagulation or RF ablation has shown the greatest impact on recent experimental and clinical research.

Radio frequency ablation (RFA) is used as minimally invasive heat-based method to ablate tumours. It is used primarily for the treatment of liver cancers but may also be employed to ablate malignant tumours of kidney, lung, bone, etc. For RFA, radio frequency waves are emitted from a generator through an non-insulated part of one or more electrodes that are inserted in the target diseased tissue. Tissue destruction in the form of coagulation necrosis is then caused primarily as a result of resistive heating in the immediate surrounding tissue and secondarily by passive heat conduction. Resistive heating only occurs within a rim of tissue in direct contact with the electrode because resistive heating is inversely proportional to the square distance between electrode(s) and tissue. Beyond this rim, tissue is further heated as a result of passive conduction. However, the RF emission is readily terminated as a result of impedance rise resulting from tissue desiccation and carbonization.

The first experiments with RFA on liver tissue were performed with a single plain metal electrode. The ablation diameter was rather limited, up to 1.6 cm, due to rapid rise in electrical impedance with current shut-off. The limited ablation diameter was insufficient to enable tumour coagulation through RFA. In order to be useful for tumour coagulation, the range of tissue destruction should cover the entire tumour and an additional rim of 1 cm of adjacent healthy tissue as a safety margin to avoid local recurrence.

The first technical challenge in the development of RFA was to design an electrode that could increase the range of coagulation lesion. Modified single-shaft electrodes have been developed and tested since 1994. In general, for different trends in the development of electrodes can be distinguished: internally cooled electrodes, expandable electrodes that enlarge the electrode-tissue interface and the electrical field, wet electrodes with saline perfusion through the electrode into the tissue, and bipolar electrodes.

In the article "Radiofrequency ablation using a new type of internally cooled electrode with an adjustable active tip: An experimental study in ex vivo and in vivo porcine livers", the authors Jihoon Cha, et al. disclose a single shaft internally cooled electrode whose exposed active tip is adjustable through a covering insulating sheet that is connected to an operator adjustable switch. The electrode with adjustable active tip length is pictured in FIG. 1 of the article of Cha et al. In vivo experiments showed that different ablation volumes could be induced by adjusting the length of the exposed active tip.

As will be explained in the following paragraphs, several problems exist with single shaft electrodes.

Firstly, the commercialised versions of the above single-shaft electrodes produce coagulations that are smaller, less predictable, less regular and less complete than assumed. This results in a high rate of up to 60% of local recurrences of the tumour due to incomplete coagulation. The use of overlapping coagulations for larger tumours is insecure with high recurrence rates as a result of persistence of skipped areas. Furthermore, tumours usually do not fit the predefined elliptical, spherical or discoid shape that is generally ablated by these single-shaft electrodes. A consequence thereof is that tumours are incompletely coagulated again resulting in high recurrence rates, or large volumes of healthy tissue surrounding the tumour are coagulated.

Secondly, apart from the wet electrodes, these electrodes have a complicated design, can be used only once, and consequently are very expensive, currently between 1000 Eur and 1500 Eur.

Thirdly, none of these electrodes serve to coagulate multiple tumours each having their own shape and size. In clinical practice however, a patient may have several tumours. As a consequence, it may be required to use more than one single-shaft electrode in the same patient to adequately treat all tumours simultaneously or sequentially.

Further, some of these electrodes like the bipolar-wet electrodes can produce very large lesions but the size and shape of the coagulated zone is unpredictable. Such excessive coagulations must be avoided to prevent damage to healthy organ tissue and noble structures in the vicinity of the tumour.

In summary, single-shaft electrodes for RFA are insufficiently reliable and safe. They are not adaptable to tumours of any size and shape in a reproducible way, cannot sufficiently safe healthy tissue and vital structures surrounding the tumour, and they are complex and expensive.

The most promising evolution in RFA is the introduction of multiple electrode devices since 2001. A multiple electrode RFA device implements the combined use of plural electrodes. Monopolar and bipolar multiple electrode RFA devices can be distinguished. In monopolar mode devices, the electric current flows from all electrodes have the same polarity towards a grounding pad. In bipolar mode devices, the electric current flows between two electrodes or a group of electrodes that have differing polarities. Further, the multiple electrode RF devices can be categorized as sequential mode, simultaneous mode, or switching mode operated. When sequentially operated, the second electrode is activated after completion of the session of the first electrode, etc. When simultaneously operated, all electrodes are active during the same time interval. In switching mode, subgroups of electrodes are activated in an alternating fashion using a switch box and controller. The following paragraphs give an overview of known multiple electrode RFA devices operated in switching mode, and their limitations.

The article "A device for radiofrequency assisted hepatic resection" from the authors D. Haemmerich, D. J. Schutt, J. A. Will, R. M. Triegel, J. G. Webster and D. M. Mahvi, describes an RFA device with 6 electrodes held in position by a Teflon guide. As is illustrated by FIG. 3, a controller (PC) and an electronic switch box activate pairs of adjacent electrodes in switching bipolar mode, 0.5 seconds per pair. As described in section II C., second paragraph, the RFA process is further monitored by the device of D. Haemmerich et al. through impedance control per electrode pair. As soon as the impedance between a pair of electrodes exceeds a certain threshold, the power supplied to this pair of electrodes is disrupted for 10 seconds.

Although the multiple electrode RFA device described in the article from D. Haemmerich et al. enables to heat large slices of tissue of even length simultaneously through the rapid switching mode, it still does not enable to reliably coagulate a tumour of given shape and size. The device is not adaptable to a variety of patterns as a result of which its usefulness for clinical practice is limited.

In another article entitled "Multipolar Radiofrequency Ablation: First Clinical Results", the authors J. Tacke, A. Mahnken, A. Roggan and R. W. Gunther describe a device with 3 electrodes inserted and held in position by aid of a plastic triangle with standardized distance control. The electrodes are saline-cooled probes that are activated pair-wise, one pair after the other, in bipolar mode. The switchbox allows for 30 possible combinations wherein the electrode pairs are alternately activated during 2 seconds each. The device of J. Tacke et al. further implements impedance control: the RF activation frequency is proportional to the tissue impedance, and if the tissue impedance increases beyond a limiting value, the coagulation process is ended.

Just like D. Haemmerich, J. Tacke et al. have disclosed a device that maximizes the achievable lesion size through a bipolar activation of multiple electrodes in switching mode, but which is not adaptable to any size or shape of a given tumour. The shape of the coagulated volume is rather pre-designed or pre-fabricated. Any deviation from the pre-fabricated shape requires multiple sequential insertions of the electrodes in the same patient, or excessive collateral destruction of healthy tissue.

In yet another article from the authors D. Haemmerich, F. T. Lee, D. J. Schutt, L. A. Sampson, J. G. Webster, J. P. Fine and D. M. Mahvi, entitled "Large-Volume Radiofrequency Ablation of ex Vivo Bovine Liver with Multiple Cooled Cluster Electrodes", a comparison is made between the sequential, simultaneous and switching mode of an RFA device with 3 cool-tip electrodes that are held in position using a Plexiglas rectangle plate. The electrodes have a fixed exposed electrode length of 2.5 cm and are operated in monopolar mode. The article demonstrates that the most uniform heating is achieved when implementing the switching mode. The device further also implements impedance feedback to turn off power for 15 seconds whenever the impedance increases to a certain extent above baseline levels.

Although D. Haemmerich et al. have demonstrated that the switching mode is advantageous in achieving a uniform heating and tissue coagulation, their device does not adapt to any size and geometry of a tumour in a controllable fashion, and their prototype device is certainly not adapted to coagulate multiple tumours in a single patient in a reliable way thereby avoiding excessive healthy tissue and organic material destruction.

International patent application WO 2004/082498 entitled "Surface Electrode Multiple Mode Operation" discloses an RFA system with a base (102) and a plurality of electrodes with adjustable penetration depth and active tip length. The insertion depth and active tip length of the electrodes are made adjustable through screwing the electrodes and sliding electrically insulating sleeves extending from the surface of the base along the electrodes. The electrodes are operated in a bipolar fashion or combinations of electrodes can be selectively placed in bipolar arrangement with each other. A bipolar configuration as such however does not guarantee accurate and predictable coagulation adaptable to any size of tumour.

European Patent Application EP 1 645 239 entitled "Cool-tip Combined Electrode Introducer" describes RFA through a system with central reference electrode and circular positioned electrodes with adjustable insertion depth and active tip length. The insertion depth is monitored and also the radio frequency ablation (RFA) process is real-time monitored through dedicated monitoring equipment like an ultrasound scanner (15) and data processor (16). EP 1 645 239 however also fails to teach how the central electrode and circular positioned electrodes have to be activated in order to enable accurate and predictable coagulation adaptable to any size of tumour.

It is an objective of the present invention to disclose a device and method for radio frequency ablation (RFA) that resolves the shortcomings of the above described devices. In particular, it is an objective to disclose an RFA device and method yielding RF coagulation of diseased tissue that is predictable and adaptable to any size or shape of tumour. It is a further objective to disclose an RFA device and method that is able to treat large, non-spherical tumours, able to treat tumours near structures that may not be destructed, and able to treat multiple tumours of different sizes and shapes in a single patient. It is an additional objective of the present invention to present an RFA device that is not complex and costly, and that can be configured in a foolproof and reproducible manner to treat one or more tumours of any size or shape.

SUMMARY OF THE INVENTION

According to the present invention, the above mentioned objectives are realized by a device for radio frequency ablation (RFA) of diseased tissue including:
  a mesh or plate with a grid of holes for holding electrodes;
  a plurality of electrodes with adaptable active tip length;
  means for visualizing and probing insertion depth of each of the electrodes in the diseased tissue;
  a switch box, connectable to the plurality of electrodes and adapted to distribute current between the plurality of electrodes during a radio frequency ablation (RFA) process;
  a control unit for controlling the switch box; and
  means for monitoring the radio frequency ablation (RFA) process,
  where the control unit is adapted to determine:
  groups of electrodes;
  an electric mode for activation of each group of electrodes;
  a polarity for electrodes within each group of electrodes;
  an activation mode for the groups;
  a time interval and order for activation of the groups;
  a power output and current strength;
  a duration of the radio frequency ablation (RFA) process,
such that each electrode is activated an amount of times such that a substantially equal radio frequency power is applied per volume diseased tissue.

Thus, the device according to the invention has multiple electrodes whose active part can be adjusted individually, and whose insertion depth can be controlled and probed individually in order to tailor the RFA coverage to the size and shape of the tumour(s) to be treated. This way, an optimal coverage of the tumour volume (plus for instance a 1 cm safety margin at each side) can be achieved enabling to effectively destruct the tumour(s), reduce the risk for recurrences, and minimize healthy tissue destruction around the tumour(s). Via the switch box and control unit, e.g. a PC that runs the operation algorithms controlling the switch box, the device according to the current invention is further designed to obtain a reliable ablation zone covering the tumour and a security margin, even if the tumour is large and/or has an irregular shape. In case of a mesh instead of a plate holding the electrodes, e.g. a nylon or silicone-like mesh, the electrodes can even be flexibly positioned thereby further enhancing the ability to adapt to the shape of the tumour(s) and/or the ability to avoid delicate structures like blood vessels. The flexibility allows for bending the mesh after insertion of an electrode to control the position of the electrode, e.g. through ultrasound. It further allows to wrinkle the mesh to adapt to the shape of the tumour.

The treatment algorithm that is run by the PC or control unit controlling the switch box is designed for optimal performance of the RFA process in order to obtain a reliable ablation zone tailored to the size and shape of the tumour. The input parameters of this algorithm may include the length of the active parts of the electrodes, the number of electrodes, the distribution pattern of electrodes in space and their inter-distance, the type of tissue, perfusion or no perfusion of the tissue, the measured impedances, etc. Based on these inputs or a subset thereof, the treatment algorithm determines which electrodes will be activated as a group, the electric mode—monopolar, bipolar, multi-polar—that will be used for activating each group, which electrodes will be activated as positive electrodes and which electrodes will be activated as negative electrodes in the bipolar mode, the activation mode—sequential, simultaneous or switching—of certain groups, the time interval for activation of each group and the order wherein the groups will be activated, the power output and current strength produced by the generator and supplied to the electrodes, the duration of the entire RFA process, etc. The algorithm determines these parameters prior to treatment or adaptively during the treatment, e.g. taking into account the impedance feedback or other parameters monitored during the RFA process. As a result of the algorithm, each electrode will be activated an equal amount of times and a substantially equal radio frequency power will be applied per volume diseased tissue in order to achieve effective and reliable coagulation of the tumour and surrounding safety margin.

Optionally, the grid of holes in the mesh or plate may have one or more of the following shapes:
 a rectangular pattern;
 a spherical pattern.

Thus, on the mesh or plate, there may be one or more patterns: rectangular 3 à 5 by 3 à 5 holes, with different inter-electrode distances, e.g. 1.5 cm, 2 cm, 3 cm, 4 cm, 5 cm. Also, a spherical grid with different inter-electrode distances may be foreseen, as well as other possible configurations. The electrodes may be arranged in clusters, e.g. triangle, square, row, or hexagon shaped clusters. The different patterns and cluster shapes further enhance the flexibility to adapt the ablation zone to the shape and size of the diseased tissue.

Optionally, the mesh or plate in the device according to the invention may have a plug per hole for connectivity with an electrode inserted in the hole, the plug being positioned around the hole.

Alternatively, the mesh or plate in the device according to the invention may have a plug per hole for connectivity with an electrode inserted in the hole, the plug being positioned near the hole.

Thus, in order to control the insertion depth of the electrodes, there may be a plug per hole or opening in the mesh or plate. The plug can be around the opening or next to it, and will be conductively connected to the electrode via an electric wire that interconnects the plug and e.g. the top of the electrode. The variant with plug around the opening is more elegant and prevents the wire from moving around. The wire is rolled up at the top of the electrode when opening the packaging and is sledded down to connect to the plug. A disadvantage of this variant is that it may be less safe regarding electric insulation of the electric contact from the patient, especially in a wet environment, e.g. with blood, saline, etc. The variant with the plug aside the opening is less elegant and enables the wire to move around. The plug and opening shall typically occupy more space on the mesh or plate which may be problematic when the electrodes are close to each other. This variant however is safer in terms of its electric insulation.

Further optionally, the mesh or plate in the device according to the invention may include:
 an electric cable connector for connectivity with the switch box; and
 electric wiring between each plug and the electric cable connector.

Indeed, for each hole and corresponding plug, there may be an electric wire that is woven into the mesh or integrated into the plate. These individually insulated wires may be combined into a single electric cable connector that leaves the mesh or plate for connectivity to the switch box. The electric cable connector enables foolproof connecting of the set of electrodes to the switch box.

According to an advantageous optional aspect the mesh or plate in the device according to the present invention or an intermediate sterile plate may include:
 a visual indicator per hole, the visual indicator being adapted to light up when an electrode is inserted in the hole, and the visual indicator further being operationally coupled to a visual indicator on the switch box, indicative for a plug on the switch box whereto the electrode has to be connected, the visual indicator on the mesh or plate and the visual indicator on the switch box enabling foolproof connectivity of the electrode to the switch box.

Thus, as an alternative to wiring and an electric cable connector integrated in the mesh or plate, visual indicators on the mesh/plate and/or visual indicators on the switch box may assist the operator of the device to foolproof connect the electrodes to the switchbox. As soon as an electrode is inserted in a hole, the corresponding visual indicator on the mesh/plate and the corresponding visual indicator on the switch box will be illuminated, enabling the operator to connect the wire attached to the electrode to the correct plug on the switch box. Apart from being foolproof, this implementation of the invention is advantageous in that the electrodes need not be connected to plugs integrated in the mesh or plate as a result of which electric insulation of the patient is guaranteed. In a more user-friendly variant, the visual indicators (e.g. LEDs) are located on an intermediate sterile plate wherein also the wiring of the electrodes can be plugged. Such intermediate sterile plate may be placed on the operation table, at a dry location on the patient, or may be held by a sterile robot arm that is fixedly mounted on the operation table to be accessible by the physician in a user-friendly manner. The intermediate sterile plate is connected to the non-sterile switch box via an electric cable connector and electric cable. The intermediate sterile plate in other words serves as an extension of the switch box user interface enabling the physician to control the switch box in a user friendly manner from within the vicinity of the operation table, whereas the non-sterile switch box can be placed away from the operation table.

In a first variant implementation, only the mesh or plate is equipped with visual indicators, e.g. LEDs. This implementation is useful in case a computer determines fully automatically, e.g. based on visual inspection and image processing, at which location the next electrode has to be inserted. The computer controls the corresponding LED on the mesh or plate to light up in order to assist the physician to foolproof insert the electrode.

In another variant implementation, only the switch box or an intermediate sterile plate that implements the user interface of the switch box is equipped with visual indicator, e.g. LEDs. The physician may for instance determine the location where the next electrode has to be inserted through ultrasound. Upon insertion of the electrode, the corresponding LED on the switch box or intermediate plate will light up enabling the physician to foolproof connect the wiring.

The visual indicator on the mesh or plate or intermediate sterile plate may consist of a colour LED.

Indeed, when using colour LEDs of different colours on the mesh or plate or intermediate sterile plate, and colour LEDs of corresponding colours on the switch box, the device according to the present invention is further improved in terms of dummy proof configuration since another level of protection against misconnection of electrodes is readily built-in this way.

Further optionally, the mesh or plate constitutes a plate and the device further comprises a robot arm for positioning the plate.

The plate will have a certain thickness, e.g. 3 to 4 cm, to guarantee parallel insertion of the electrodes. The plate can be put directly on the organ that needs to be treated, e.g. the liver, or more preferably is held by a robot arm. The robot arm may be fixed on the operation table. The robot arm enables to hold the plate steady at the desired position and orientation, e.g. 5 cm above the organ to be treated, such that all electrodes can be inserted parallel and sufficient space is left for e.g. an ultrasound probe that is used to control the insertion depth and position of the electrodes in the diseased tissue. The electrodes are inserted manually.

Further optionally, the device may comprise a robot arm for positioning the plurality of electrodes substantially parallel to each other.

Indeed, a robot arm the end of which consists of a plate preloaded with e.g. 5 by 5 electrodes may be positioned manually or by navigation onto the organ to be treated, e.g. the liver. Once the end of the robot arm is in place at the surface of the organ to be treated, e.g. the liver, each of the electrodes is driven out by a mechanism that forms part of the robot arm itself, for a predetermined insertion depth. Also the length of sheeting of the individual electrodes, in case of electrodes with adaptive insulating sheets as described below, may be obtained mechanically, i.e. by a mechanism in the robot arm itself instead of manually. The number and position of the electrodes, the lengths of insertion and the lengths of the sheeting can be determined either by individual electronic commands from the physician or fully automated, based on imaging pre- and per-operatively. The electrodes may be wire-connected to the switch box in one of the ways described above.

According to another optional aspect, each electrode of the plurality of electrodes has a sliding electrically insulating sheet for adapting the active tip length.

Thus, the length of the active part of the electrodes may be individually adaptable by sliding an insulating sheet, e.g. made of plastic, over the electrode till the sheet is within 1 cm of reach of the anterior border of the tumour. When this is done after the electrode has been inserted to a depth of 1 cm beyond the inferior border of the tumour, the length of the active part of the electrode shall correspond to the thickness of the tumour issue at the location where the electrode is inserted plus a 1 cm safety margin at each side of the tumour. When this procedure is followed for each electrode, it is clear that the length of the active part shall differ between electrodes inserted in the same tumour depending on the local thickness of the tumour. Consequently, an optimal coverage of the whole tumour volume will be achieved, perfectly adapted to any size or shape of tumour.

Further optionally, the electrically insulating sheet may be coated with a coating that is better visible through ultrasound.

Such coated sheet would enable to monitor the sliding of the insulating sheet over the electrode through ultrasound. This way, sliding the sheet to the correct position, i.e. till the sheet is within 1 cm of reach of the anterior border of the tumour, would become less prone to human errors which can still occur in the alternate solution where the sliding is for instance done based on grade marks on the electrodes.

According to another advantageous, optional aspect of the RFA device, one or more of the plurality of electrodes are partially shielded along their circumference for directing the RF field generated thereby near the border of the diseased tissue.

Indeed, when using plain electrodes in bipolar or multi-polar mode, a rim of tissue of 0 à 1 cm is coagulated outside the volume created by interconnecting the outer electrodes. In order to avoid such unwanted coagulation outside the volume created by the outer electrodes, these outer electrodes can be partially shielded, e.g. over 180° of their circumference, with an insulating sheet. The insulating sheet may for instance be made of plastic. As a result, the rim of unwanted coagulation will be inexistent or will be much narrower.

Further optionally, each partially shielded electrode may have a shape that obstructs rotating the partially shielded electrode once inserted in said diseased tissue.

Thus, to prevent outer electrodes that are partially shielded along a portion of their circumference to rotate once inserted in the tissue, these electrodes may be given a directional shape that obstructs such rotation. The directional shape may be a blade shape, or may consist of small wing-shaped extensions that prevent a circular electrode from rotating once inserted in the tissue. If the partially shielded outer electrodes would rotate, the effect of reducing unwanted coagulation outside the volume created by the outer electrodes could disappear or at least be non-optimal.

The plurality of electrodes optionally may have differing lengths.

Thus, as an alternative to electrodes with a sliding insulating sheet, the length of the active part of an electrode could be adapted to the local thickness of the tumour by selecting an electrode with the correct active length before inserting the electrode. This way, the ablation zone could be adapted to the size and shape of the tumour such that the whole tumour volume plus a safety margin is perfectly covered.

Further optionally the means for monitoring in the RFA device according to the present invention may include:
 a ground plate; and
 means for measuring impedance between the ground plate and respectively each electrode of the plurality of electrodes.

The ground plate may be put onto a part of the patient's body at a certain distance from the electrodes, typically on the thigh in case of liver treatment. The ground plate will serve to measure electrical impedance between each individual electrode and the ground plate either before or at regular time intervals during the RFA process. As will be explained below, the impedance measurement may assist in calculating the insertion depth or active part length of each electrode, enables to check which positions in the grid of holes are occupied with electrodes, and allows to monitor the coagulation process in order to interrupt, stop or control the ablation process.

Alternatively, the means for monitoring in the RFA device according to the present invention may include:
  means for measuring impedance between respective pairs of the plurality of electrodes.

Thus, in an alternative implementation, the ground plate can be avoided and impedance measurements can be done between pairs of electrodes. The impedance can be measured at a standard frequency of 500 kHz or a frequency below or above.

According to another alternative, the means for monitoring in the RFA device according to the present invention may include:
  means for measuring impedance between a reference electrode and respectively each non-reference electrode of the plurality of electrodes.

In this variant implementation, a ground plate is also avoided and a reference electrode is introduced to assist in the impedance measurements. Again, the impedance can be measured at a standard frequency of 500 kHz or a frequency below or above. The impedance can be measured during insertion of an electrode in the tissue. Since diseased tissue and healthy tissue have different impedances, the curve representing the variation in impedance during insertion of the electrode will show an important change at the point where the electrode tip enters the diseased tissue, and a second important change at the point where the electrode tip leaves the diseased tissue. These points may be used by the physician to determine the insertion depth of the electrode, or may serve to light up a LED or other visual indicator that are indicative to the physician. The reference electrode itself may have two zones, a first zone near the tip and a second zone along the shaft, in between which the impedance is measured upon insertion. The changes in variation of the impedance will then indicate when the tip of the reference electrode enters the tumour and leaves the tumour.

Further optionally, the device according to the invention may further include one or more of the following:
  means for transforming the impedance into information indicative for positions in the mesh or plate that are occupied;
  means for transforming the impedance into information indicative for the active tip length of each electrode;
  means for transforming the impedance into information indicative for progress of the radio frequency ablation (RFA) process; and
  means for transforming the impedance into information indicative for verification of the coagulation after the radio frequency ablation (RFA) process.

Measuring the pre-treatment impedance, either between pairs of electrodes, between electrodes and a ground plate or between electrodes and a reference electrode, allows to verify which positions in the grid of holes are occupied by an electrode and which are not. In the latter case, the measured impedance will in theory be infinitely large. Pre-treatment impedance measurement may also enable to calculate the active tip length of an electrode. When it is assumed that the pre-treatment intrinsic impedance of healthy tissue is substantially equal, and the pre-treatment intrinsic impedance of diseased tissue is also substantially equal but higher than that of healthy tissue, then the changes in measured impedance during insertion of an electrode are due only to the length of the electrode part that is exposed to diseased tissue. The impedance shall start rising upon entry of the electrode tip in the tumour near the anterior border and shall start decreasing as soon as the electrode tip leaves the tumour at the inferior border. Similarly, measuring the impedance intermittently during the ablation process allows 2D or 3D monitoring of the progress of the ablation process since the impedance will rise as a result of coagulation of tissue. Sufficiently high impedance may indicate that the target tissue has been devitalised and may allow to temporarily interrupt and to timely stop the ablation either locally or entirely. At last, post-treatment impedance measurements may indicate the presence of diseased/healthy tissue or allow verifying the degree of coagulation. In case of presence of diseased tissue, the tumour has not yet been ablated completely and the RFA treatment must be repeated or continued.

Further optionally, the control unit may be adapted to activate a group of electrodes during successive cycles alternating in centrifugal and centripetal mode.

Indeed, in case of rows with equal polarity, i.e. one row with positive-positive-positive- . . . electrodes and one row with negative-negative-negative- . . . electrodes, the central part in between the group of electrodes will be less coagulated as a result of the Faraday effect. In case of rows with alternating polarity, i.e. one row with positive-negative-positive- . . . electrodes and one row with negative-positive-negative- . . . electrodes, the central part in between the electrodes will be over-coagulated as a result of the centripetal current. Therefore, in a preferred embodiment, the algorithm controlling the switch box controls a single group of electrodes to alternate during successive cycles between the centrifugal scheme with rows having electrodes of equal polarity and the centripetal scheme with rows having electrodes of alternating polarity.

Optionally, the device according to the invention may further include:
  means for logging parameters prior to and during the radio frequency ablation (RFA) process.

Indeed, a PC for instance allows to log different parameters before and throughout the procedure: current, power, impedance, position and length of the electrodes, etc. These parameters are stored, can be visualized graphically, can be printed or kept in the patient's medical record, etc.

The device according to the invention may further optionally include:
  means for visualizing via a two dimensional (2D) representation and colours responsive to impedance measurements, the progress of the radio frequency ablation (RFA) process.

Indeed, a 2D representation on a screen can visualize the position of the electrodes, e.g. represented by a dot, as well as the area that is covered by each electrode, e.g. represented by a square or circle. The colour of the square or circle may represent the impedance measured locally. The colour scale may vary from 0 Ohms up to for instance three times the pre-treatment impedance or up to a fixed value of e.g. 300 Ohms in order to maximise visibility of impedance change during the ablation process. The square or circle of unoccupied electrode positions may be represented in black. The numerical value of the measured impedance may be shown for each square or circle, or may not be shown, or may be shown upon mouse-clicking or touching the square or circle.

Alternatively, the device according to the invention may further include:
  means for visualizing via a three dimensional (3D) representation taking into account the active tip lengths of said electrodes and colours responsive to impedance measurements, the progress of the radio frequency ablation (RFA) process.

Indeed, on the screen a third dimension can be added based on the length of the active part of each electrode. The squares or circles are then replaced with bars or ellipsoidal volumes whose length corresponds to the length of the active part. The virtual image obtained this way can be fused with a 3D representation of the tumour such that the position of the electrodes and the progress of the ablation process can be monitored visually on the screen.

Further optionally, the device according to the invention may include an RF control interface for the switch box and/or a power unit.

Such RF control device enables distributed control of the switch box and/or power generator. The RF control device serves as an extension to the switch box or generator user interface and may for instance be integrated in a sterile plate or housing for use by the physician on or near the operation table. A single RF controller may be provided per switch, connected to a bus, and controlled from a master controller.

In addition to an RFA device, the current invention also applies to a corresponding method for treatment of diseased tissue through radio frequency ablation (RFA), the method including the steps of:

providing a mesh or plate with a grid of holes for holding electrodes;
inserting a plurality of electrodes with adaptable active tip length in the holes;
visualizing and probing insertion depth of each of the electrodes in the diseased tissue;
connecting the plurality of electrodes to a switch box;
controlling the switch box for distributing current between the plurality of electrodes during a radio frequency ablation (RFA) process; and
monitoring the radio frequency ablation (RFA) process, where controlling the switch box comprises determining:
groups of electrodes;
an electric mode for activation of each group of electrodes;
a polarity for electrodes within each group of electrodes;
an activation mode for the groups;
a time interval and order for activation of the groups;
a power output and current strength;
a duration of the radio frequency ablation (RFA) process, such that each electrode is activated an amount of times such that a substantially equal radio frequency power is applied per volume diseased tissue.

The diseased tissue subject to the method according to the invention may comprise a brain tumour in which case the electrodes are stiff needles.

Indeed, in particular for brain tumours where the margin for coagulation is very small and edema outside the coagulation zone could cause overpressure and edema resulting in intracranial hypertension, very accurate and predictable control of the ablation zone, tailored to the size and shape of the (smaller) brain tumour, is essential and achievable through the switch box control algorithm according to the present invention. An embodiment of the present invention wherein the electrodes are miniaturized and kept rigid in order to avoid deformation when inserted in the soft brain tissue, i.e. an embodiment wherein a matrix of needle electrodes is used, could overcome the medical communities' prejudice that radio frequency ablation is not applicable to brain tumours.

Preferably, the method according to the current invention applied to brain tumours includes:

pre-operative imaging;
determining orientation, insertion depth and active tip length of the needle electrodes in function of an optimal insertion path determined during the pre-operative imaging;
creating a pre-fabricated cluster of needle electrodes taking into account the orientation, insertion depth and active tip length; and
inserting the pre-fabricated cluster of needle electrodes robot-wise into the brain tumour.

Thus, when applied to brain tumours, the method according to the invention preferably makes use of a pre-fabricated cluster of needle electrodes that are inserted simultaneously into the brain by a robot. Whereas such pre-fabricated cluster of needles is less preferable for treating diseased tissue in larger organs such as the liver, longs or kidneys because of the moving membrane of these organs, the pre-fabricated cluster of needle electrodes is advantageous for treating brain tumours because it avoids uncontrolled relative movement of needle electrodes inserted in the soft brain tissue.

Alternatively, the method according to the current invention applied to brain tumours includes:

pre-operative imaging;
determining orientation, insertion depth and active tip length of the needle electrodes in function of an optimal insertion path determined during the pre-operative imaging;
sequentially inserting the needle electrodes robot-wise into the brain tumour, taking into account the orientation, insertion depth and active tip length.

When inserted one by one, the method according to the invention applied to brain tumours preferably comprises using an intermediate plate that maintains the needle electrodes in position during sequential insertion thereof.

The method according to the current invention, applied to brain tumours and using a robot to insert the needle electrodes simultaneously or sequentially, preferably includes referring a robot coordinate system to a brain coordinate system for localizing the brain tumour during insertion of the needle electrodes.

The method according to the current invention, applied to brain tumours and using a robot to insert the needle electrodes simultaneously or sequentially, as defined by claim 29 preferably comprises referring a robot coordinate system to a brain coordinate system for localizing the brain tumour during insertion of the needle electrodes.

The localizing mechanism hence has to relate a 3D brain or tumour coordinate system to a 3D robot coordinate system. This may be realized using conventional localizing mechanisms either based on target references mounted on the patient's skull and visualized through MRI, three LEDs and a pellet visualized through MRI, fitting or matching skill patterns visualized through regular cameras, etc.

The method according the invention applied to brain tumours may further include:

temperature monitoring and feedback; and
controlling the radio frequency ablation (RFA) process thereby maintaining the temperature below 60° C.

Such slow ablation based on temperature monitoring and feedback allows to reduce heat diffusion in the brain and to avoid carbonisation around the electrodes. the temperature sensors may be inserted separately or may alternatively be combined with/integrated in the needle electrodes.

According to a further optional aspect, the method according to the invention may include using one or more cooling electrodes for bordering the radio frequency ablation zone.

In particular when applied for treatment of brain tumours near important nerves, veins or other brain structures, these structures may be protected from ablation through the use of one or more cooling electrodes that form a cage delimiting the ablation zone. Also the use of partially shielded needle electrodes, e.g. along the border or in corners of the ablation zone, may be advantageous in treatment of brain tumours in order to further improve controlling and delimiting the ablation zone.

The method may use electrodes of differing thickness. One example thereof is an embodiment with central thick electrode(s) surrounded by thin, needle electrodes.

BRIEF DESCRIPTION OF THE DRAWINGS

FIG. 1A illustrates a mesh or plate with a rectangular pattern of holes for holding electrodes in an embodiment of the RFA device according to the invention;

FIG. 1B illustrates a mesh or plate with a spherical pattern of holes for holding electrodes in an embodiment of the RFA device according to the invention;

FIG. 7 illustrates an activation scheme for 3 by 3 electrodes with groups of 2 by 2 electrodes;

FIG. 8 illustrates an activation scheme for 4 by 3 electrodes with groups of 3 by 2 electrodes;

FIG. 9 illustrates an activation scheme for 3 by 3 electrodes with groups of 3 by 2 electrodes;

FIG. 10 illustrates centrifugal polarity in the activation scheme of FIG. 9;

FIG. 11 illustrates centripetal polarity in the activation scheme of FIG. 9;

FIG. 12 illustrates an activation scheme for 4 by 4 electrodes with groups of 4 by 2 electrodes;

FIG. 19 illustrates coagulation outside the zone surrounded by the electrodes in an embodiment of the present invention;

FIG. 20 illustrates a partially shielded electrode for use in an advantageous embodiment of the RFA device according to the invention; and FIG. 21 illustrates coagulation outside the zone surrounded by the electrodes in an embodiment of the present invention wherein the partially shielded electrode of FIG. 20 is used.

DETAILED DESCRIPTION OF EMBODIMENT(S)

Figure 2B:
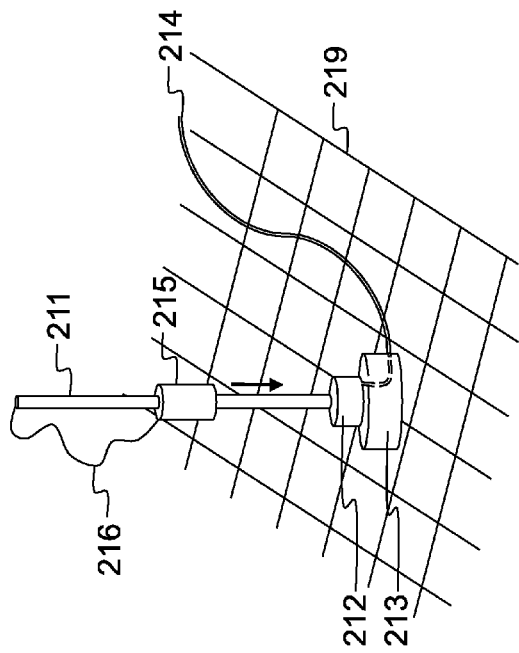
FIG. 2B illustrates the insertion of an electrode in the hole drawn in FIG. 2A.

A preferred embodiment for tailored radio frequency ablation (RFA) according to the invention consists of the integrated combination of:
a mesh or plate with a pattern of electrode guides, electric connectors and an integrated electric circuit;
plural adjustable electrodes;
an adjustable guiding device;
a ground plate;
a switch box:
a personal computer (PC) with:
operation algorithms;
logging of the procedure;
visualisation of the position of the electrodes, their impedance, active length, and activation status (positive or negative);
introduction of data, menu;
an electric generator that allows power up to 500 W and that can work with low impedance.

FIG. 1A and FIG. 1B illustrate implementations of the mesh or plate with a pattern of electrode guides, electric connectors and an integrated electric circuit. Thanks to the mesh or plate multiple electrodes can be arranged in fixed clusters, e.g. triangle, square, row, or hexagon shaped clusters. Alternatively, they can be inserted through a block with parallel perforations. Such a block is useful for ex vivo experiments but is less useful for treatment of a patient because the block is heavy and cumbersome. A block (and also a plate) do not allow a flexible positioning of the electrodes to adapt for the shape of the tumour or flexible positioning in order to avoid delicate structures like blood vessels. Manual positioning of the electrodes is very flexible, but does not guarantee parallel insertion in a very regular equidistant pattern. In addition, since there is one electric cable for each electrode, the numerous cables easily get mixed up. The multiple cables at the end of the different electrodes also tend to bend these electrodes. A lot of attention has to be paid to correctly connect the cables one by one to the right connector at the generator (or to the switch box between the electrodes and the generator). This is a time consuming task that must be executed carefully by the operator or physician. One mistake can ruin the result of the treatment.

In the preferred embodiment of the invention, this problem is resolved by using a synthetic mesh, e.g. made of nylon, with the consistency of a piece of cloth without memory such as plastic and not elastic yet very flexible, e.g. cotton. Alternatively, the mesh can be a silicone-like transparent or opaque flexible mesh.

In the mesh or plate, a grid of holes is foreseen for insertion of the electrodes. Advantageously, there will be several patterns like for instance a rectangular grid with 3 to 5 holes by 3 to 5 holes, with different inter-electrode distances, e.g. 1.5 cm, 2 cm, 3 cm, 4 cm, 5 cm; as well as a spherical grid with different inter-electrode distances, and other possible configurations. FIG. 1A illustrates a mesh 100 with rectangular grid of holes 101 whereas FIG. 1B illustrates a mesh 110 with spherical grid of holes 111.

The flexibility allows for bending the mesh or plate after insertion of an electrode in such a way that its position can be controlled and monitored through ultrasound. The flexibility also enables to wrinkle the mesh or plate to adapt for the shape of the tumour or in order to avoid delicate structures e.g. blood vessels.

Figure 2D:
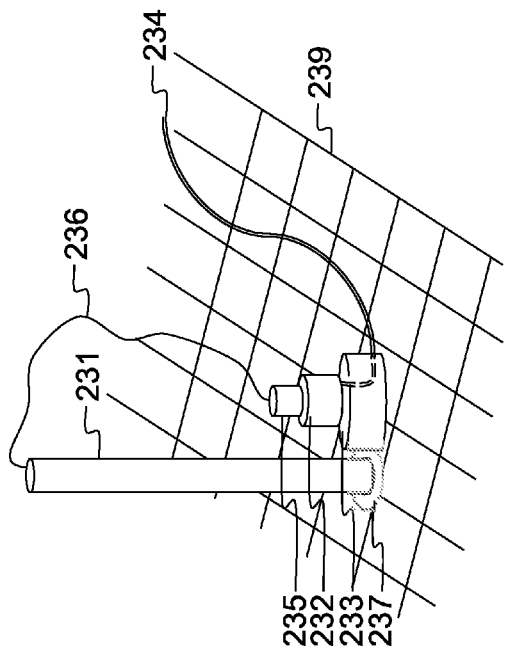
FIG. 2D illustrates the insertion of an electrode in the hole drawn in FIG. 2D.
Figure 2A:
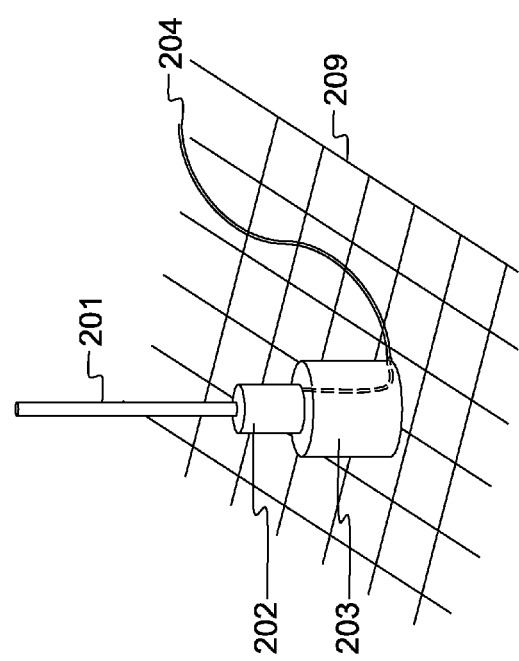
FIG. 2A illustrates a hole with plug around the hole in an embodiment of the RFA device according to the invention.
Figure 2C:
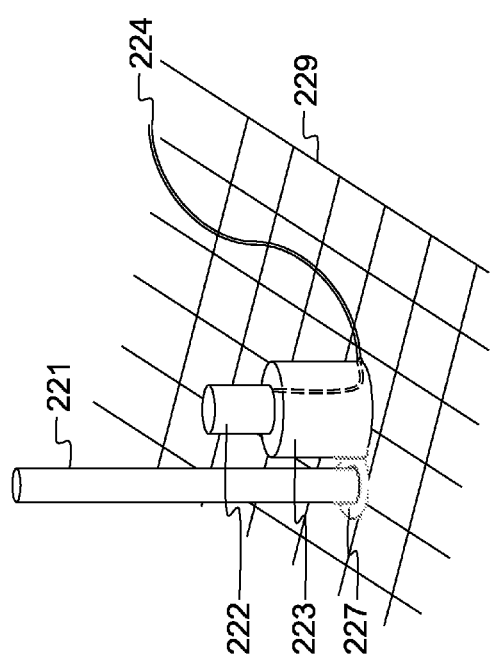
FIG. 2C illustrates a hole with plug near the hole in an alternative embodiment of the RFA device according to the invention.

For each opening in the mesh or plate, a plug is attached to or integrated in the mesh or plate. The plug can be located around the opening as is illustrated by FIG. 2A and FIG. 2B or the plug may be located just next to the corresponding hole as is shown in FIG. 2C and FIG. 2D.

The implementation with plug, 202+203 or 212+213, around the opening is more elegant because it consumes less space and the wire 216 moves less around. It is noticed that the plug consists of a plastic part, 203 or 213, and a metal part, 202 or 212, that is electrically conductive. A plug 215 and the wire 216 may be rolled up at the top of the electrode, 201 or 211, when opening the packaging. The plug 215 is then sledded down to connect to the conductive part, 202 or 212, of the plug integrated in the mesh or plate, 209 or 219. FIG. 2A and FIG. B further show the wiring, 204 or 214, integrated in the mesh or plate. The wiring may be used also to control LED indicators integrated in the mesh or located on an intermediate sterile plate or on the switch box front panel to assist the physician in foolproof connecting the electrodes.

The implementation with plug, 222+223 or 232+233, near the opening, 227 or 237, is somewhat less elegant because the wire 236 can more easily move around and the opening and plug occupy more space. The latter may be a problem especially when the electrodes are close to each other. It is noticed again that the plug consists of a plastic part, 223 or 233, and a metal part, 222 or 232, that is electrically conductive. The wire 236 extending from the top of the electrode, 221 or 231, is terminated at a plug 235 that connects to the conductive part, 222 or 232, of the plug integrated in the mesh or plate. The version with plug near the corresponding hole is safer regarding electric insulation and exactly measuring the depth taking into account the height of the mesh or plate is no problem. FIG. 2C and FIG. D further show the wiring, 224 or 234, integrated in the mesh or plate, 229 or 239.

Figure 3:
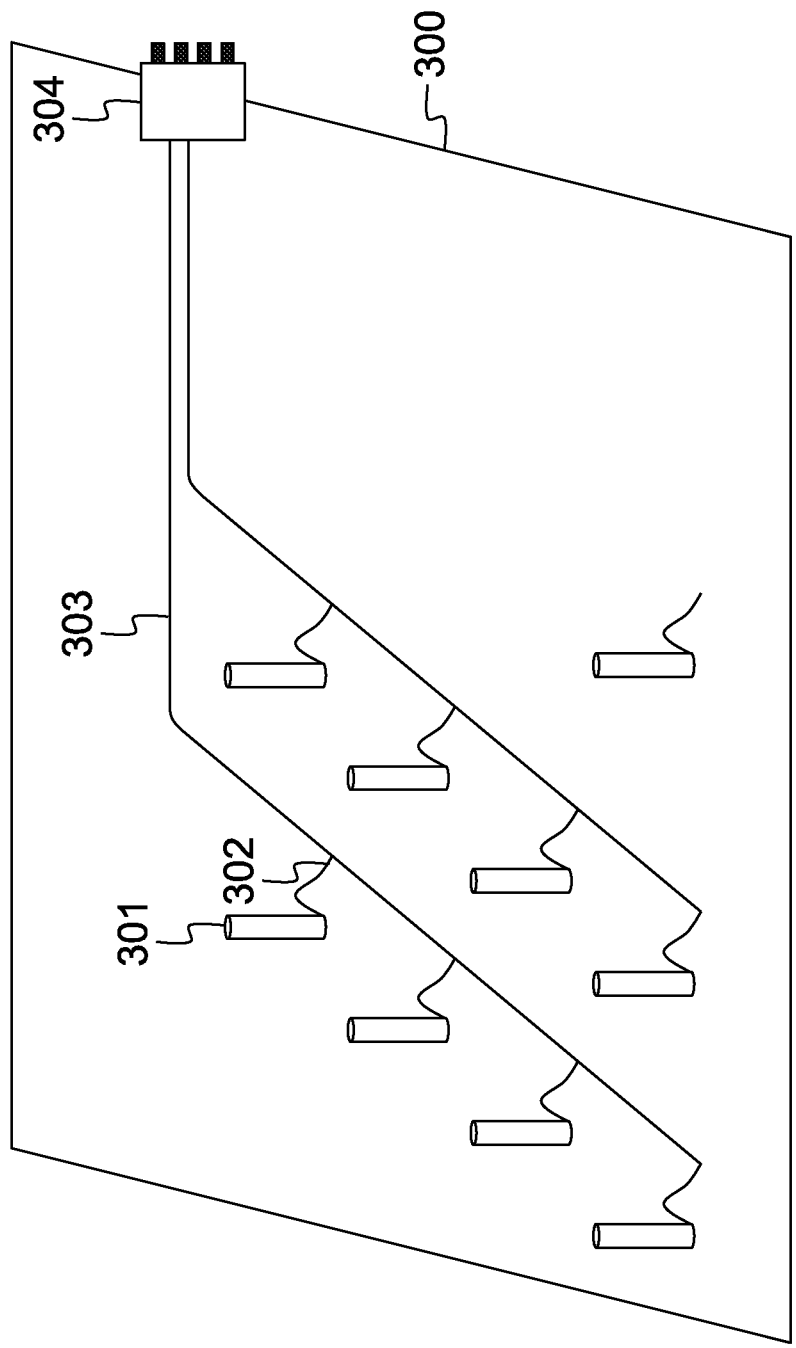
FIG. 3 illustrates a mesh or plate with integrated wiring and electrical cable connector in an embodiment of the RFA device according to the invention.

As is illustrated by FIG. 3, an electric wire, 302 and 303, is woven into the mesh or integrated into the plate 300 for each hole and corresponding plug 301. These individually insulated wires are combined into a single electric cable connector 304 that leaves the mesh or plate 300 and that is connected to the switch box.

Figure 4B:
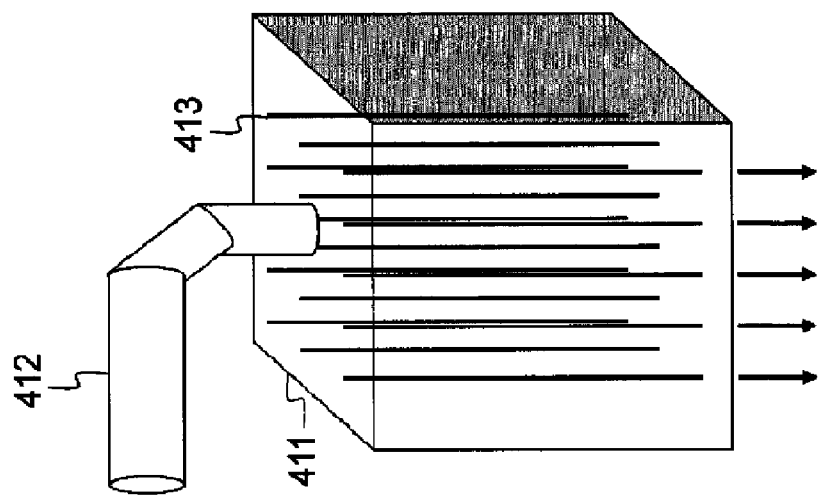
FIG. 4B illustrates an embodiment of the RFA device according to the invention with motorized robot arm.
Figure 4A:
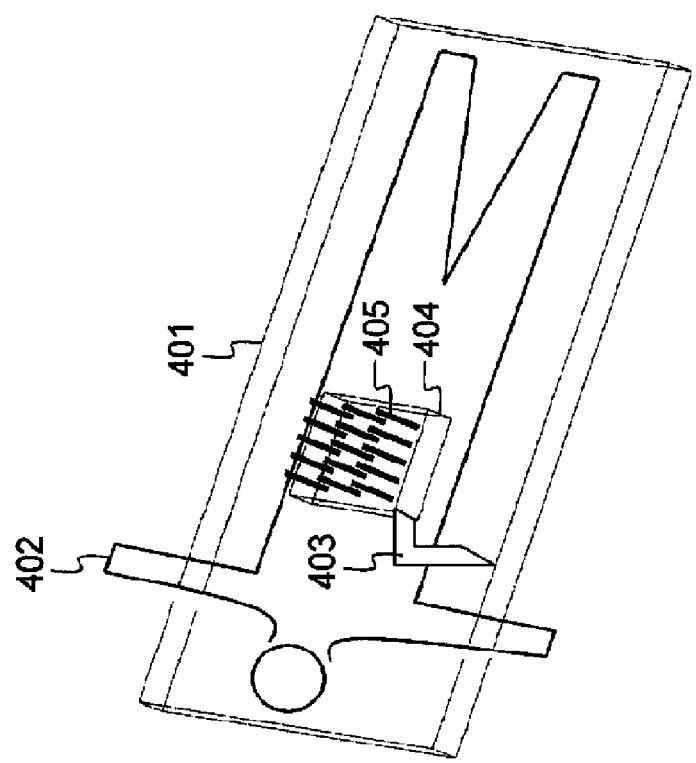
FIG. 4A illustrates an embodiment of the RFA device according to the invention with plate and robot arm.

As an alternative to a flexible mesh or plate, the electrodes 405 can be sledded through a multi-perforated plate 404 with a hole e.g. every cm, as is illustrated by FIG. 4A. The plate 404 can be solid, with drilled holes, or hollow, with small tubes connecting the upper and lower surface of the plate. Alternatively, the upper or lower surface plate can be left out provided that the plate and the small tubes are rigid enough to guarantee parallel insertion. All holes have an electric plug and electric wiring but not all holes need to be used for the RFA procedure. This plate 404 has a certain thickness, e.g. 3 to 4 cm, to guarantee parallel insertion of the electrodes. The plate can be put directly onto the organ of the patient 402 that needs to be treated, e.g. the liver. More preferably, the plate 404 is held by a robot arm 403 that is fixedly mounted on the operation table 401. Such robot arm 403 allows to hold the plate 404 steady in the desired location and orientation, typically 5 cm above the organ to be treated, such that all electrodes 405 can be inserted parallel and sufficient space is left for an ultrasound probe to control the insertion depth and position of the electrodes 405. The robot arm 403 is moved manually into the desired position. Alternatively, the robot arm 403 may be equipped with position measurement means.

FIG. 4B shows a variant embodiment with a fully automated robot arm 412 the end of which consists of a plate 411 preloaded with electrodes 413. The robot arm 412 is positioned by navigation onto the organ to be treated, e.g. the liver. This robot arm 412 is equipped with a position measurement system and motor for automatically moving the arm 412 and electrodes 413. The electrodes 413 are driven out by a motorized mechanism that forms part of the robot arm 412 itself. The depth of insertion is based on pre- and per-operative imaging of the tumour and the tumour-bearing organ. The electrodes are wired in a similar fashion as described above.

Figure 5:
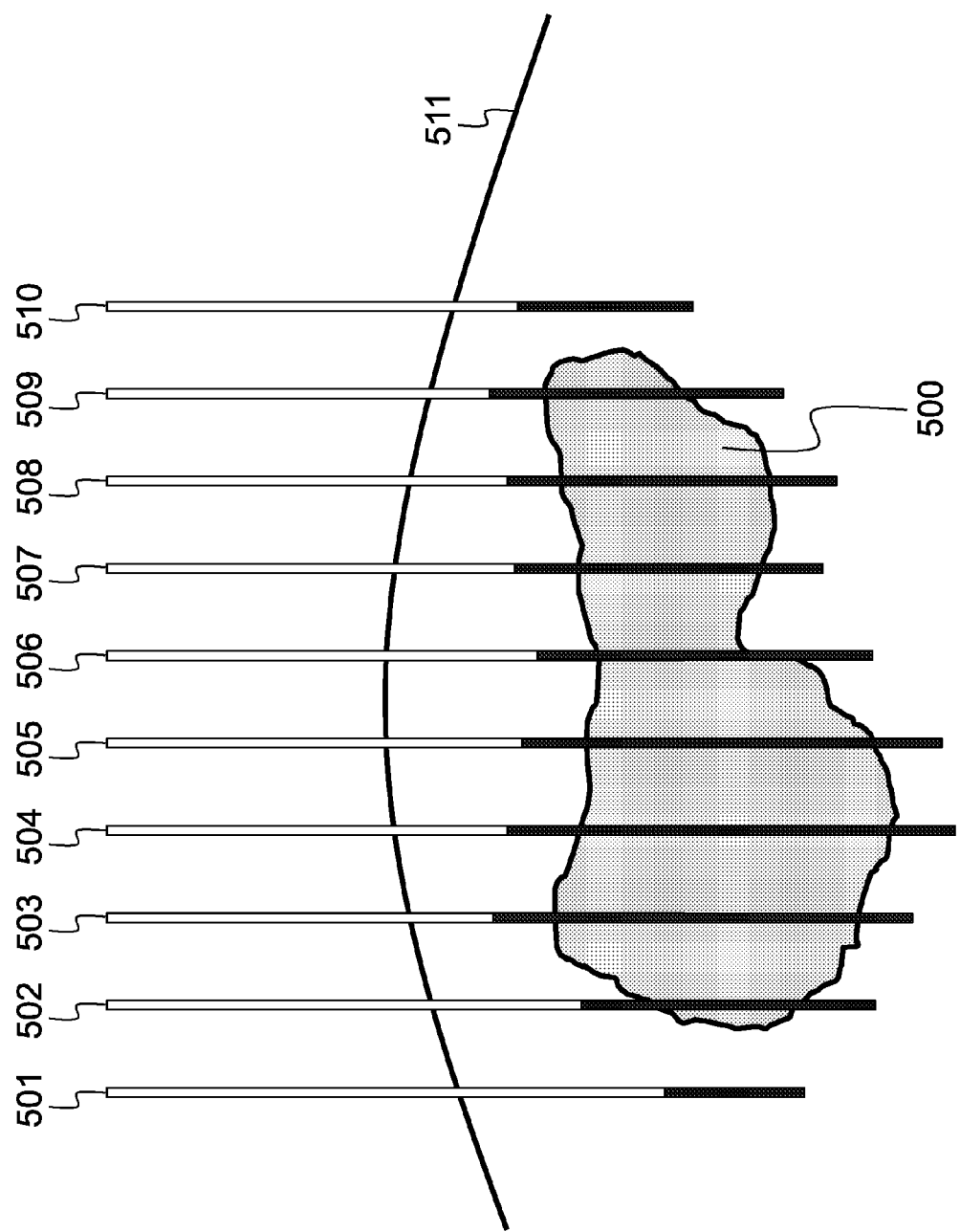
FIG. 5 illustrates the electrodes with adaptable active part length in an embodiment of the RFA device according to the invention.
Figure 6:
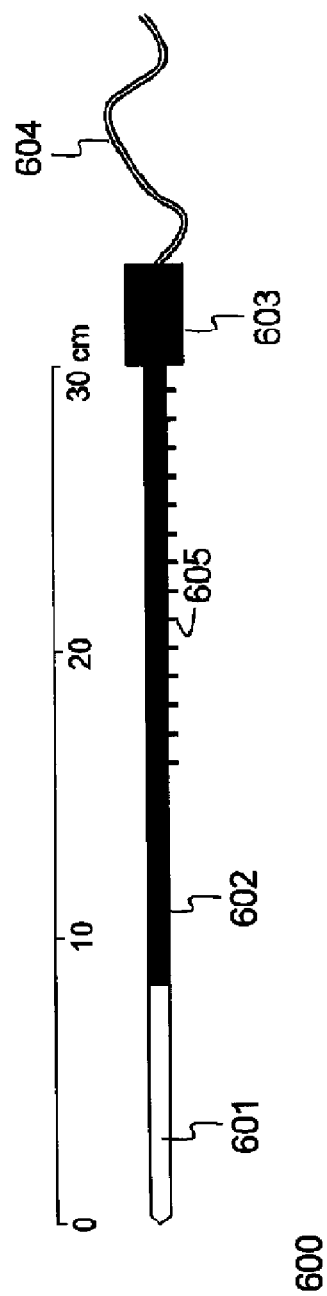
FIG. 6 illustrates an electrode with gliding sheet as used in the embodiment of the RFA device illustrated by FIG. 5.

The length of the active part of the electrodes preferably corresponds to the thickness of the tumour tissue 500 at the location of the electrode plus a 1 cm safety margin at both sides. This is illustrated by FIG. 5 for a number of electrodes, 501, 502, 503, 504, 505, 506, 507, 508, 509, 510, that are used in an RFA process for treating the liver tumour 500 of a patient 511. The active tip length 601 of the electrodes is adaptable by gliding an insulating plastic sheet 602 over the electrode until this sheet is within 1 cm of reach of the anterior border of the tumour. This is illustrated in FIG. 5 by the upper part of the electrodes that is left white. Prior to sliding the sheet 602, the electrode 600 must be inserted to the preferred depth, i.e. 1 cm below the inferior border of the tumour. Insertion of the electrode 600 to the preferred depth and sliding the sheet to the preferred depth may be done using ultrasound or a variant technology for visualization of the electrode. FIG. 6 further shows the handle 603, wiring 604 and markings 605 on the electrode that may assist in sliding the insulating sheet 602 to the appropriate depth.

Alternatively, in simple cases with a limited number of electrodes, the length of these electrodes may differ and the physician may choose for each location an electrode with the right active length before inserting the electrode.

The length of the active part may differ between electrodes inserted in the same tumour according to the local thickness. As a result, an optimal covering of the whole tumour volume 500 is achieved, perfectly adaptable to each size and shape.

In case of insertion of the electrodes through the pre-wired mesh or plate, a passive robot arm can be used to ensure that the electrodes are perfectly parallel to each other. The adjustable guiding device allows insertion of the electrodes with minimal interference with ultrasound guidance and despite pace constraints in a patient.

A ground plate is put onto a part of the body of the patient at a certain distance from the electrodes, typically onto the thigh. It will be used to measure electrical impedance between each individual electrode and the ground plate either before or at regular time intervals during the ablation process, or both. Such impedance measurement gives a threefold kind of information:

> When it is assumed that the pre-treatment intrinsic impedance of the tissue is equal for all electrode positions, and that the distance from each electrode to the ground plate is roughly equal, the difference in measured impedance is resulting from the difference in length of the exposed electrode tip. The impedance shall decrease linearly with increasing length of the exposed tip. The PC can thus easily calculate the length of each electrode.

> Measuring the pre-treatment impedance also allows to check which positions in the grid are being occupied by an electrode and which are not. In the latter case, the impedance will be infinitely high.

> Measuring the impedance intermittently during the ablation process further allows 2D or 3D visual monitoring of the RF process and allows to stop the ablation when a sufficiently high impedance indicates that all targeted tissue has been devitalised.

The switch box that forms part of the device according to the current invention can stand alone or can be integrated with the generator. The switchbox receives the combined electric wiring coming from the mesh or plate. It allows a spatial control of the multiple electrodes. The switch box thereto contains hardware that allows redistribution of the current over and between the different electrodes. It also contains a variable electric resistance that can be incorporated into the circuit in order to instantaneously modify the current that actually flows between certain electrode pairs at certain moments.

As already indicated above, the RFA device according to the invention preferably contains a PC with:

operation algorithms;

logging of the procedure;

visualisation of the position of the electrodes, their impedance, active length, and activation status (positive or negative);

introduction of data, menu.

The PC enables to steer the ablation process by controlling or commanding the switch box. In a possible implementation of the RFA device, the basic current is set on the front panel of the generator. In an alternative version of the RFA device, the PC also controls the basic current of the generator. Initially, the PC commands a pre-treatment cycle with a small electric current that runs between each individual electrode and the ground plate. This enables the PC to obtain information on the length of each electrode. It also allows the PC to check which positions in the grid are being occupied by an electrode and which are not. The PC further runs the operation algorithms that will be described in the following paragraphs.

The PC further runs the operation algorithms. These treatment algorithms are designed for optimal performance of the radio frequency electrodes in order to obtain a reliable and tailor-made ablation zone covering the tumour and a safety margin surrounding the tumour, even if the tumour is large or if its shape is irregular. The parameters of the treatment algorithm can be pre-set or can be adapted manually.

The operation algorithm is based on the following pre-radio frequency input parameters:

the length of the non-insulated part of the electrodes;

the number of electrodes;

the distribution of the electrodes in space, i.e. the pattern and the inter-electrode distance;

the type of tissue; and the perfusion of the tissue or the absence thereof.

The operation algorithm may further be based on the following input parameter measured during radio frequency application:

the impedance between electrodes and ground plate; or the impedance between electrodes and a reference electrode; or the impedance between pairs of electrodes.

The operation algorithm determines the following output parameters:

the electrodes that will be activated as a group;

the electric mode by which each group of electrodes is activated, i.e. monopolar or bipolar;

which electrodes will be activated as positive and which will be activated as negative electrodes in the bipolar mode;

the activation mode of the electrodes, i.e. either sequential, simultaneous or switching mode;

in case of switching mode, the time interval of activation of each group of electrodes and the order in which the groups are activated in a circular movement;

the power output and current strength; and the duration of total ablation procedure.

Based on experimental studies with multiple electrodes in ex-vivo beef liver, an example algorithm has been developed. Therein, the use of four parallel plain 3 cm electrodes arranged in a square pattern with a bipolar current between the 2 rows of 2 electrodes, each row being electrically connected in parallel, showed to result in very reliable and reproducible, complete coagulation of the area in between the electrodes with a 3-5 mm coagulation outside the area in between the electrodes. Thereto, the inter-electrode distance was selected to be 2 cm or less, the power was selected to be 60 W or less, the power was applied until impedance rise with automatic power shut-off rather than using an algorithm with a predefined, fixed duration. The resulting duration of the coagulation was in between 6 and 8 minutes.

The experiments showed that the bipolar mode between two groups of electrodes was more efficient and reliable than a simultaneous monopolar activation of the same four electrodes due to the Faraday effect, a consecutive monopolar activation of the same four electrodes, or a consecutive bipolar activation of the same four electrodes.

Further, it was learned experimentally that the ideal power necessary for coagulation of the area between four similar electrodes with a non-insulated length of L cm equals 60 Watt×L/3.

The experiments further showed that the switching mode was more efficient than a consecutive mode wherein a first cube and than a second cube is activated to consecutively coagulate two neighbouring cubes of tissue, determined by two rows of three electrodes whereof the second electrode in each row belongs to both the first and the second cube. Indeed, in the consecutive mode, the tissue in the neighbourhood of the electrodes common to both cubes will be completely dehydrated after coagulation of the first cube. This will prevent a correct current flow in the second cube. Apart from being more efficient, the switching mode also works faster than the consecutive mode.

Similarly, the experiments showed that the switching mode is more efficient than a simultaneous mode. In such simultaneous mode, the current is diluted over a larger volume which may cause a problem for large tumours. In addition, in the simultaneous mode, the current is pushed away towards the borders of the volume occupied by the electrodes due to the Faraday effect. As a result, the rim of unnecessary coagulation surrounding the desired treatment volume is enlarged. The resulting coagulation in other words is less reliable and predictable in the simultaneous mode.

In a preferred implementation of the current invention, the electrodes are inserted into the tumour, parallel to each other, in a rectangular pattern with an inter-electrode distance of 2 cm. The whole tumour and a safety margin of 1 cm are covered. In case an electrode of the rectangular pattern would fall outside the covered area, the flexibility of the mesh or plate is exploited to put the electrode nearer to fall just within the area. The length of the electrodes is adapted to the local thickness of the tumour with a safety margin of 1 cm above the anterior or upper border of the tumour and a safety margin of 1 cm below the inferior or lower border of the tumour. Depending on their position relative to the tumour, three types of electrodes can be distinguished: corner electrodes that are in contact with healthy tissue in two directions, side electrodes that are in contact with healthy tissue in one direction, and central electrodes that have no contact with healthy tissue. Tissue is sufficiently coagulated when the impedance between central electrodes has increased by a factor 2 à 3. Corner electrodes maintain a lower impedance since they stay in contact with healthy tissue in two directions. For side electrodes, an intermediate impedance rise is noticed. In case of homogeneous coagulation, the impedance remains substantially constant throughout the treatment up to the point of complete coagulation where a sudden increase in impedance is noticed. As a general principle, blocks of electrodes will be activated following a particular scheme such that all electrodes have been activated an equal amount of time. A number of schemes that respect this general principle will be described in the following paragraphs with reference to FIG. 7, FIG. 8, FIG. 9, FIG. 10, FIG. 11 and FIG. 12 respectively.

Figures 7, 8, 9:
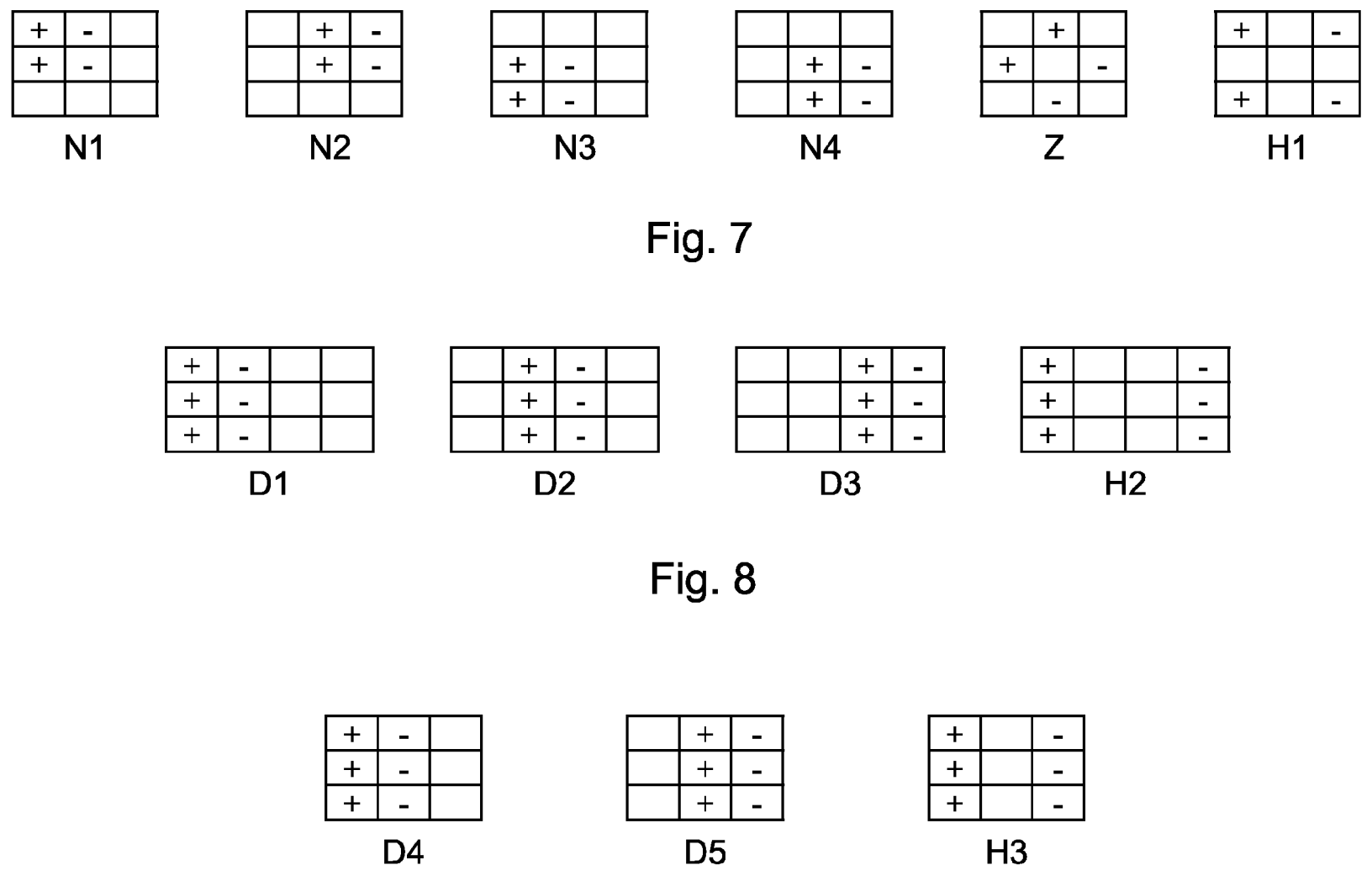

In case of 3 by 3 electrodes, and groups of 2 by 2 electrodes, FIG. 7 illustrates a scheme wherein 4 normal activation patterns N1, N2, N3 and N4 are used once, an activation pattern Z that compensates for the lower activation of side electrodes versus central electrodes is used twice, and an activation pattern H1 that compensates for the lower activation of the corner electrodes versus the central electrodes is used three times. A complete cycle consists of 9 sequential activations: H1-Z-N1-H1-N2-Z-H1-N3-N4.

In case of 4 by 3 electrodes, there is no solution with groups of 2 by 2 electrodes. FIG. 8 illustrates a solution with groups of 3 by 2 electrodes wherein 3 normal activation patterns D1, D2 and D3 are used once, and an activation pattern H2 that compensates for the lower activation of corner electrodes is used once. A complete cycle consists of 4 sequential activations: D1-D2-D3-H2.

FIG. 9 illustrates a similar activation scheme for 3 by 3 electrodes with groups of 3 by 2 electrodes. Two normal activation patterns D4 and D5 are followed by an activation pattern H3 that compensates for the lower activation of the corner electrodes. A complete cycle in this case consists of 4 sequential activations: D4-D5-H3. Groups of 3 by 2 electrodes are advantageous in comparison to groups of 2 by 2 electrodes because the impedance will be lower, current intensity will be higher and coagulation will be faster. In case of 3 by 2 electrodes, a more powerful generator may be required.

Figures 10, 11, 12:
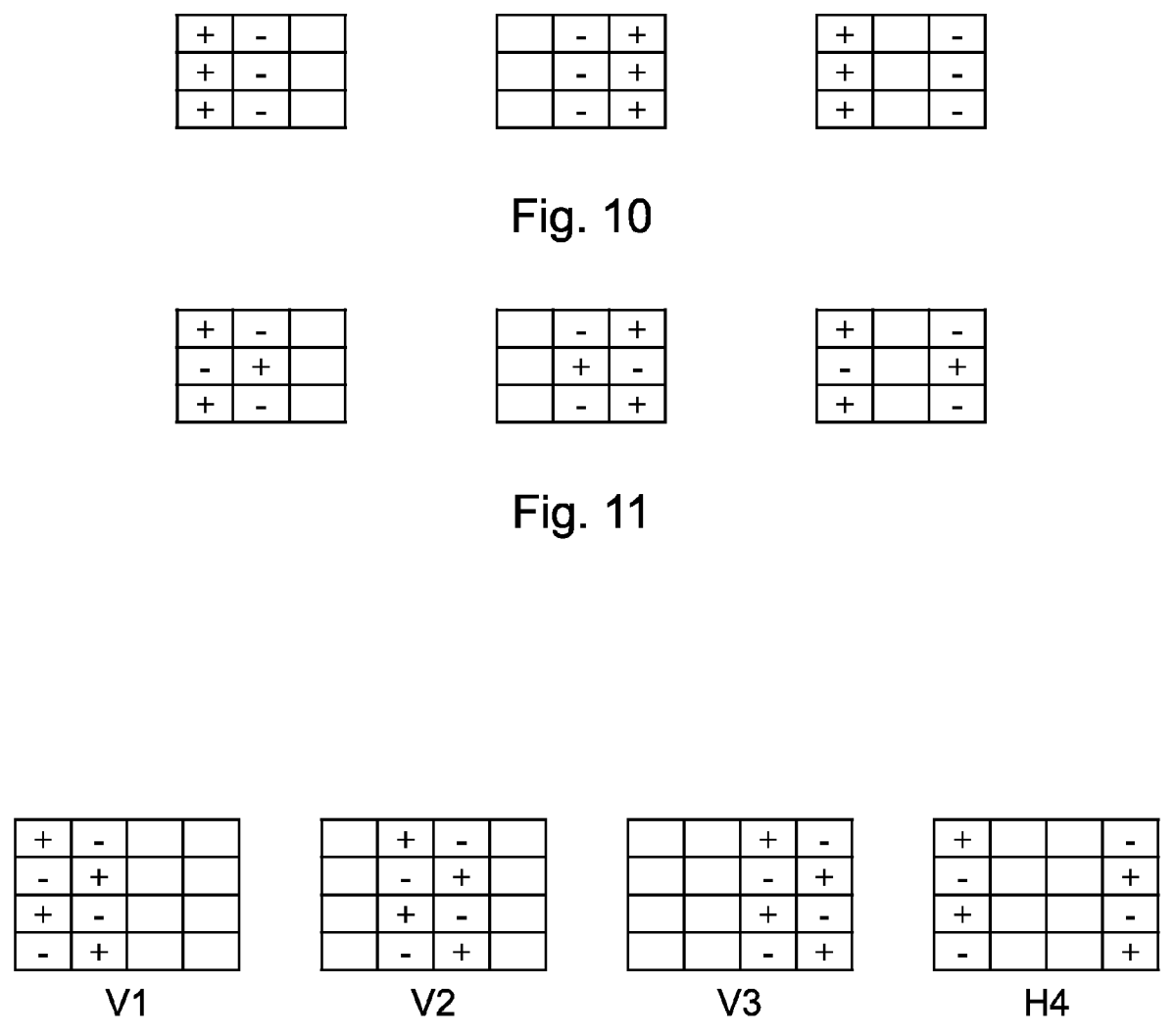

In case a row of 3 positive electrodes and a row of 3 negative electrodes is used, the central part in between the rows of electrodes is less coagulated because of the Faraday effect. In case of alternating rows, i.e. one row with positive-negative-positive electrodes and one row with negative-positive-negative electrodes, the central part in between the electrodes is over-coagulated as a result of the centripetal current. The solution to this problem lies in alternation between the centrifugal scheme with rows having electrodes of equal polarity as is illustrated by FIG. 10 and the centripetal scheme with rows having electrodes of alternating polarity as is illustrated by FIG. 11. This principle applies to both situations with 3 by 3 electrodes and situations with 3 by 4 electrodes.

In case of 4 by 4 electrodes, FIG. 12 illustrates an activation scheme with groups of 4 by 2 electrodes. Three normal activation patterns V1, V2 and V3 are followed by an activation pattern H4 that compensates for the lower activation of corner electrodes. A complete cycle consists of 4 sequential activations: V1-V2-V3-H4. The centripetal cycle illustrated by FIG. 11 will be followed by a centrifugal cycle.

In summary, x by y electrodes can be activated in rows in order to obtain homogeneous coagulation. A row in this case contains x or y electrodes, whichever is largest. This way, the coagulation speed is increased and a large distance between corner electrodes that have to be activated separately is avoided. A more powerful generator however is required in order to be able to activate the rows of electrodes. In case of a less powerful generator the other direction can be considered wherein each row contains x or y electrodes, whichever is the smallest. In the first half cycle, a row pattern is followed wherein groups of two neighbouring rows are activated, one group after the other. A centripetal polarisation scheme is used, i.e. each row contains either positive or negative electrodes. In order to compensate for the lower activation of the corner electrodes, an additional activation of a group constituted by the first and last row of electrodes is executed. In the second half cycle, the centrifugal equivalent is gone through.

As soon as the impedance is larger than 25 Ohms, the generator is switched off. In case longer electrodes are used and/or the inter-electrode distance decreases and/or more electrodes are activated simultaneously, the impedance shall decrease and a more powerful generator is needed. The generator is also switched off as soon as the switch frequency becomes higher than $1/200$ milliseconds. The ideal switch interval resides between 200 milliseconds and 500 milliseconds. In order to obtain a homogeneous coagulation within the area surrounded by the outer electrodes without burning effect, the ideal energy density is 4.2 à 5 Watt/cm$^3$.

Figure 13:
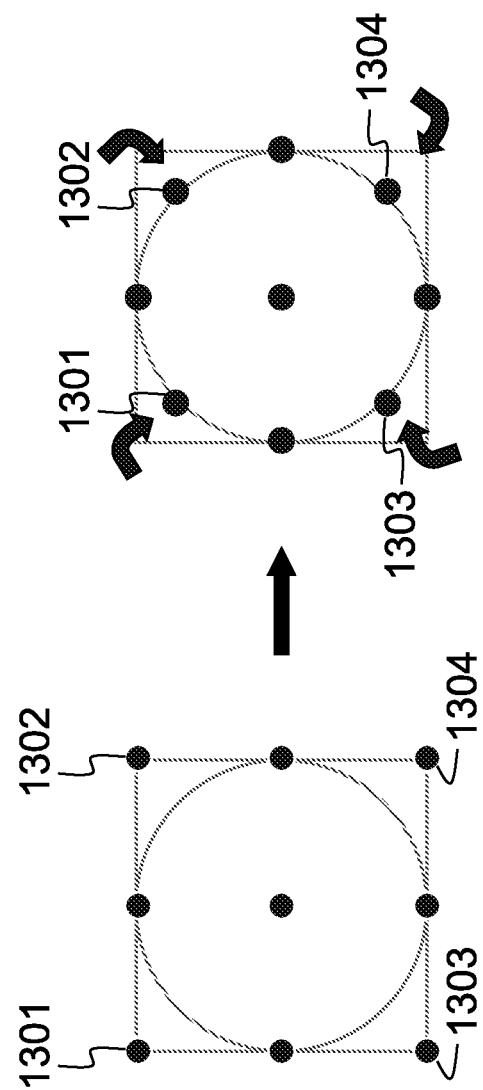
FIG. 13 illustrates the positioning of electrodes in case of a sphere or cylinder volume to be coagulated.

FIG. 13 illustrates the positioning of electrodes in case of a sphere or cylinder to be coagulated. Compared to a square or rectangle, the corner electrodes, 1301, 1302, 1303 and 1304, are moved inside. The electrodes are then activated as if they still form part of the square or rectangle. This scheme works for a sphere with radius R where the central electrode has an active tip length 2R and the circumferential electrodes have a length of $2/3$ R. The inter-electrode distance equals R. The scheme is also useful in case of a cylinder with radius R and height h. The inter-electrode distance in this case equals R and the length of the active tip of all electrodes equals h. In case neighbouring electrodes have different active tip lengths, the shortest active tip length must at least equal $2/3$ of the longer active tip length. Otherwise, coagulation might be incomplete.

Figure 14:
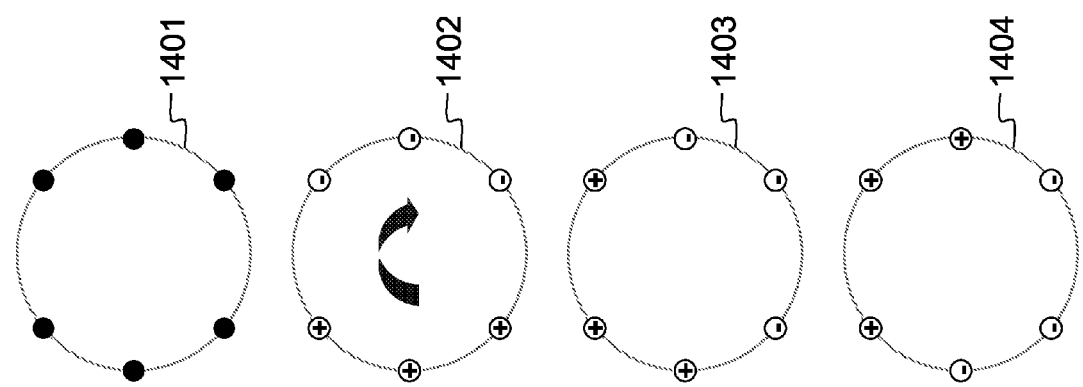
FIG. 14 illustrates an alternate positioning and activation scheme in case of a cylinder volume to be coagulated.

As is illustrated by FIG. 14, a cylinder volume can also be coagulated using a scheme 1401 with 6 instead of 9 electrodes, i.e. a scheme without central electrode. Three electrodes have a positive polarity, three electrodes have a negative polarity. The set of electrodes with positive polarity cyclically alternates as is illustrated in FIG. 14 by the subsequent schemes 1402, 1403 and 1404. The inter-electrode distance can at most be $2/3$ of the electrode's active tip length h.

Figure 15:
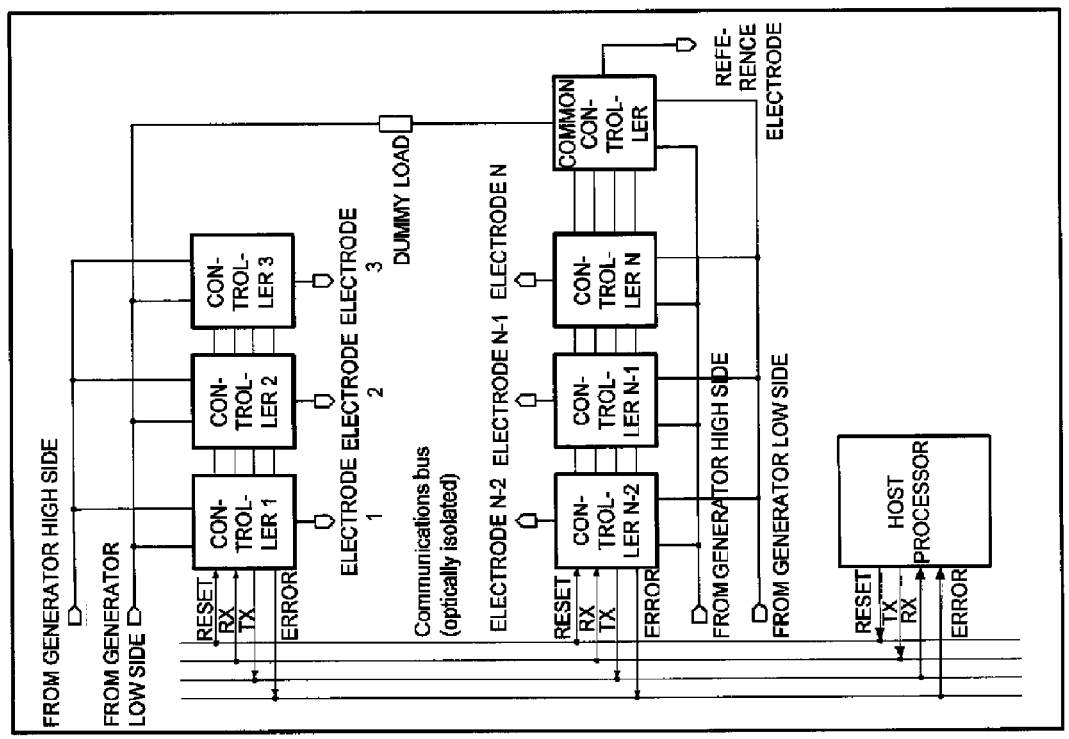
FIG. 15 illustrates an embodiment of the switch box in an RFA device according to the current invention.

FIG. 15 gives an overview of the different elements in a preferred embodiment of the switch box that forms part of the present invention. Each switch is connected to an electrode that is inserted into the tissue. All switches share a connection with the high and low output of a power generator. The common controller in FIG. 15 drives a dummy load. It measures the commonly applied generator voltage and connects the reference electrode during impedance measurements. The host processor controls all the distributed controllers via the optically isolated communications bus. This is the only place where the actual notion of a matrix exists. The dummy load is also controlled from this central location. To apply energy to the tissue the host processor controls the switches such that e.g. adjacent electrodes are connected to opposite polarities of the generator, allowing current flow through the tissue. In order to measure the tissue impedance the current flow is preferably measured between one electrode and a reference electrode or plate. When measuring with respect to a common reference electrode, the measurement is independent of the impedance of the neighboring electrodes. During application of energy to the tissue, the reference electrode is disconnected to avoid current leakage to this electrode. To perform the impedance measurement, the same current can be used as is used for the treatment but it will only be applied a fraction of the time needed for tissue ablation. The amount of energy, which corresponds to the applied power multiplied with time, will be proportionally lower due to the short measurement time. Due to the common nature of the reference electrode the current measurement could be performed in the common controller as well. This could simplify all other electrodes by eliminating the current measurement circuitry from them. However the local measurement can also be used during energy application to the tissue as a means to verify correct operation or to shut down an electrode in case of severe over-current. The same common controller that connects to the reference electrode also performs the voltage measurement needed to calculate the impedance of every node. It also connects the dummy load to the output of the generator when no other switch is activated.

Figure 16:
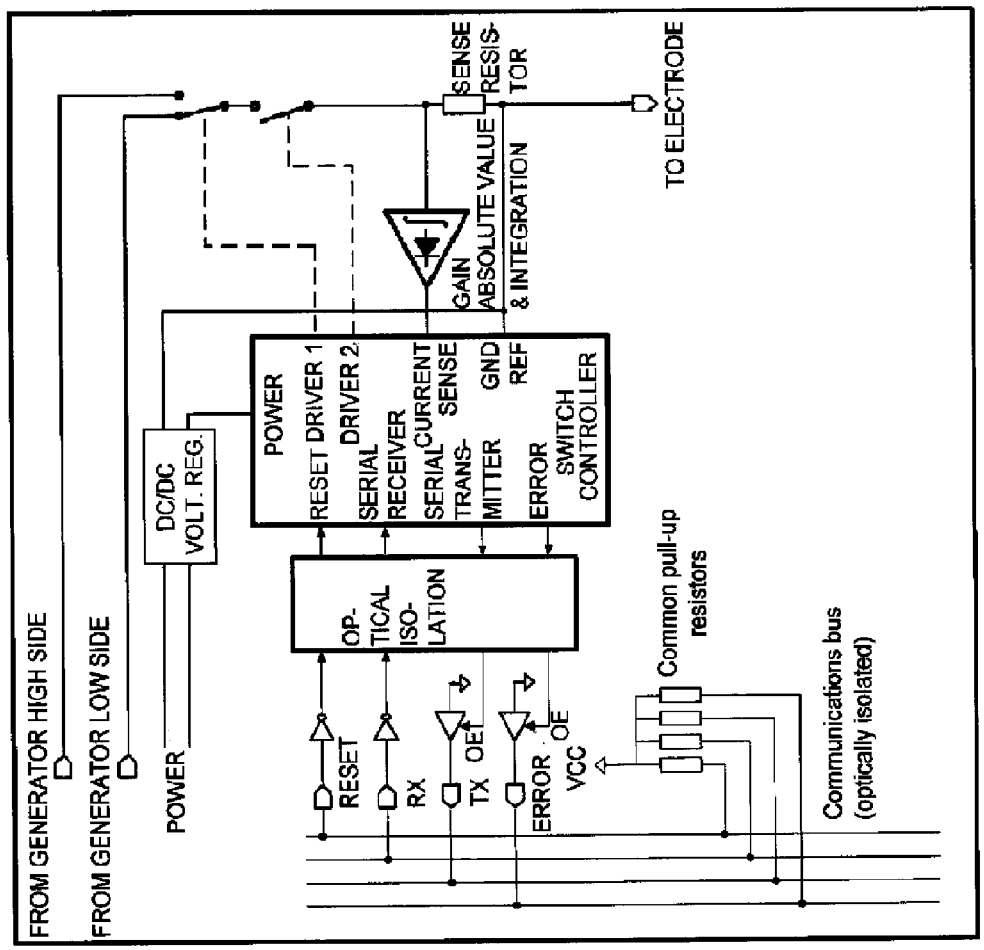
FIG. 16 illustrates connectivity of a single switch to the communications bus in the embodiment of the switch box illustrated by FIG. 15.

FIG. 16 illustrates a single switch connected via optical isolators to the common communications bus. All switches consist of identical hardware and software, the only difference being the address value allowing them to identify the messages that are directed to them.

The switch box can be built using electromechanical relays. Instead of bulky mechanical relays with limited lifetime, MOSFETs can be considered. MOSFETs however are no perfect isolators at the relatively high output frequency of the generator. Even low-leakage MOSFETs with a parasitic capacitor between drain and source in the order of 40 pF cause a significant amount of power to between the high and low output of the generator. Building an AC switch using MOSFETs places two of these devices in series, effectively increasing the overall impedance to 16 kΩ. These values are high compared to the on-state resistance which is in the order of 0.1Ω. However connecting a large amount of these devices in parallel like in a 5×5 matrix, the combined impedance drops to 640Ω. This means that a significant fraction of the generator's output power is dissipated in the MOSFETs and does not contribute to the ablation process: a more powerful generator would be needed. With the current state of power MOSFETs it is not practical to implement such a large switch matrix without wasting a lot of output power. Small, high-endurance relays can be used to overcome the leakage issue until MOSFETs with lower leakage become available.

The matrix structure is virtual: all distributed processors share a common serial communications bus. Each processor is uniquely identified by a distinct address on this bus. The matrix concept only exists in the host processor that maps the addresses onto a two-dimensional matrix via a lookup table.

Local micro-controllers are used to control the switches. They share a common serial data bus line as well as a common reset and error line. Communication takes place in a half-duplex way. Each slave node is constantly monitoring the data line driven by the master or host. When a command is addressed to the switch controller, it only reacts if it recognizes its address. Depending on the command, the controller activates or deactivates its output, or it sends status and measurement information to the host. All serial interfaces share common open-drain lines with common pull-up resistors. Since the ground reference of each switch is floating, the communications interface must be optically isolated from the host processor and from the other nodes.

An asynchronous serial interface is used to connect the processors to a common bus and to the host processor. The communication speed is not critical since not all nodes have to be configured simultaneously nor will they all report their measurement information at the same time. Only switches that are turned on and actively conduct current will perform current measurements and are requested to send these values over the communications bus. It is only during the identification phase that the entire matrix needs to be scanned.

The generator needs a minimum load resistor. The common controller connects a 1 kΩ dummy load resistor across the output of the generator during the time that no other switch is active in order to avoid that the generator goes in to self-protective mode. The combination of this dummy load and the common voltage measurement allows the intact reuse of the electrode switch circuit boards for this purpose. The control of the dummy load must be handled by the host processor since this is the only point where the state of each electrode is known.

The PC allows logging the different parameters before and throughout the procedure: the current, the power, the measured impedance values, the positions occupied by the electrodes, the active part length of these electrodes, etc. These parameters are stored and can be visualized in a graph. They can be printed or stored in the patient's medical record.

During the RFA treatment the position of the electrodes, their impedance, the active part length, and the activation status may be visualized in a two-dimensional (2D) or three-dimensional (3D) representation on screen, e.g. the PC screen.

Figure 17:
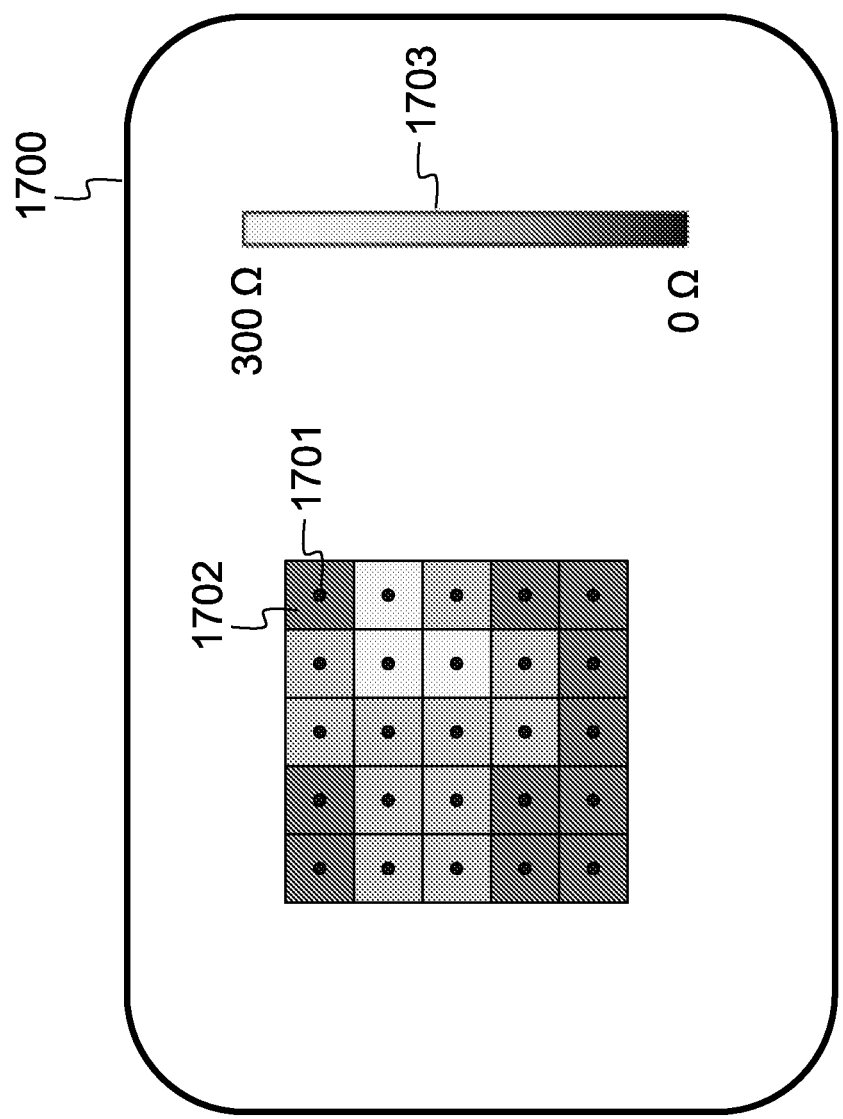
FIG. 17 illustrates a two-dimensional (2D) visualization on screen of the RFA process in an embodiment of the invention.

As is shown by FIG. 17, the PC screen 1700 can visualise the position of the electrodes, represented by a dot 1701, and the area that is controlled by each electrode, represented by a square 1702, in a 2D fashion. The colour of the square may be representative for the measured impedance. The colour scale varies from zero Ohm to for instance three times the pre-treatment impedance, or alternatively to a fixed value of e.g. 300 Ohm in order to maximise visibility of impedance change during the ablation process. This is indicated by colour scale 1703 on the screen 1700. The squares representing electrode positions that are not occupied by electrodes are coloured black. For each square, a numerical value indicative for the measured impedance can be shown or not on the screen, or the value can be shown by mouse-clicking onto the square. The colours of the squares are coded, e.g. red, green or black. As an example, a black colour may mean that the electrode is not active, a green colour may mean that the electrode functions as a positive electrode in a bipolar electric mode, and a red colour may mean that the electrode functions as a negative electrode in a bipolar electric mode. This way, the correct activation of the electrode groups can be monitored visually.

Figure 18:
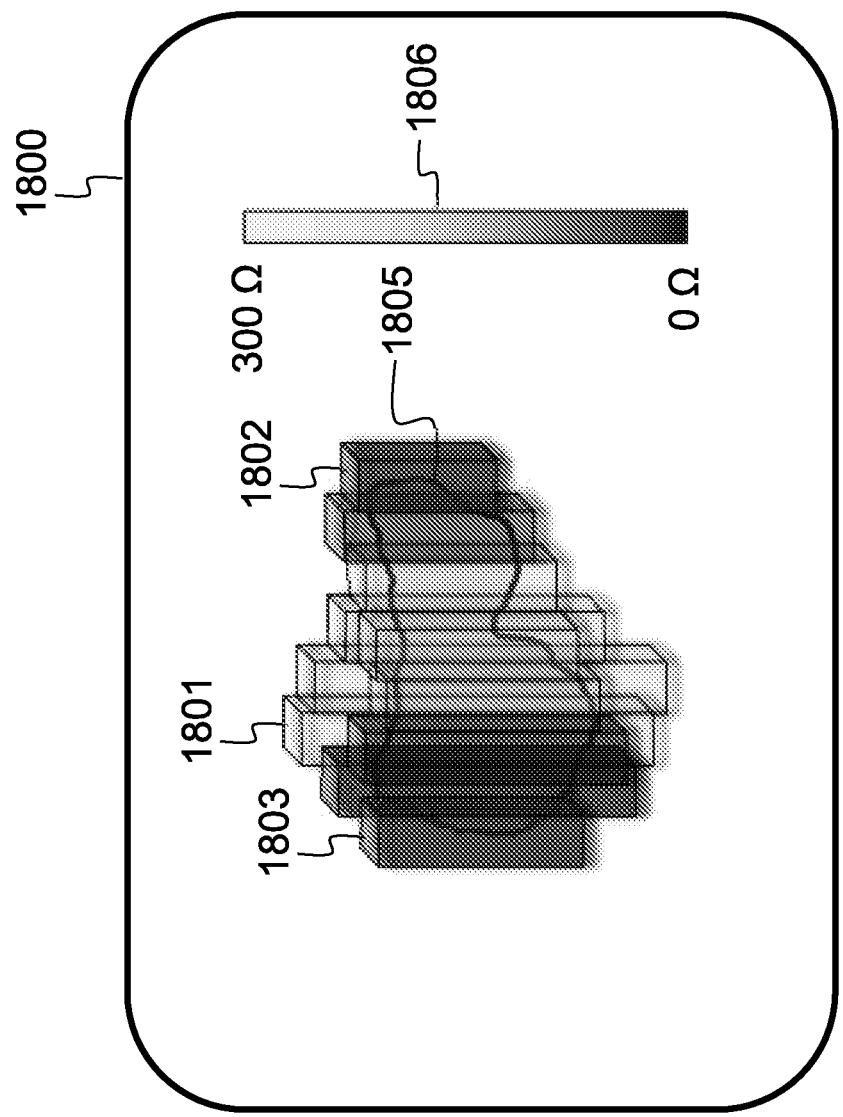
FIG. 18 illustrates a illustrates a three-dimensional (3D) visualization on screen of the RFA process in a alternative embodiment of the invention.

As is further illustrated by FIG. 18 the PC screen 1800 can add a third dimension based on the length of the non-insulated part of each electrode. The squares are then replaced by bars, e.g. 1801, 1802, 1803, that follow the axis of the respective electrodes. The screen 1800 further shows a colour scale 1806 that ranges from 0 to 300 Ohms.

The so obtained 2D or 3D virtual image can be fused with a 2D or 3D imaging of the tumour 1805, such that the position of the electrodes and the progress of the ablation process can be monitored visually. This is illustrated by FIG. 18.

The PC further allows easy introduction of patient data like name, date of birth, and other patient related information, for storing purposes. The PC thereto provides an easy to use menu that allows to choose between the different functions.

The generator in the RFA device according to the invention can be commercially available or purpose-made. Preferably, it enables powering up to 500 Watt and it should be able to work with low impedance.

With plain electrodes 1901, 1902, 1903 and 1904 used in bipolar or multipolar mode, a rim 1905 of tissue of 0 to 1 cm is coagulated outside the volume surrounded by the outer electrodes. This is due to the current that arrives at the electrodes from the outside, as illustrated by FIG. 19. In order to avoid this unwanted coagulation 1905 outside the volume surrounded by the outer electrodes, the outer electrodes can be partially shielded by an insulating sheet or coating, e.g. a plastic sheet 2002, typically over 180°. Such partially shielded electrode 2001 is shown in FIG. 20. As a result, no or a substantially narrower rim of unwanted coagulation outside the electrode cage will persist. This is illustrated by FIG. 21 which shows the coagulation zone 2105 in case four partially shielded corner electrodes 2101, 2102, 2103 and 2104 are used.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", "third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A device for radio frequency ablation (RFA) of diseased tissue, comprising:
    a mesh or plate with a grid of holes for holding electrodes;
    a plurality of electrodes with adaptable active tip length;
    means for visualizing and probing insertion depth of each of said electrodes in said diseased tissue;
    a switch box, connectable to said plurality of electrodes and adapted to distribute current between said plurality of electrodes during a radio frequency ablation (RFA) process;
    a control unit for controlling said switch box; and
    means for monitoring said radio frequency ablation (RFA) process;
    wherein a plurality of said holes of said grid are occupied with electrodes arranged in rows and said control unit is adapted to determine:
        groups of electrodes;
        an electric mode for activation of each group of electrodes; and
        a polarity for electrodes within each group of electrodes, wherein said control unit is adapted to activate a group of electrodes during successive cycles alternating in centrifugal mode with rows having electrodes of equal polarity and centripetal mode with rows having electrodes of alternating polarity;
        an activation mode for the groups;
        a time interval and order for activation of the groups;
        a power output and current strength;
        a duration of the radio frequency ablation (RFA) process,
        whereby each electrode is activated an amount of times such that a substantially equal radio frequency power is applied per volume diseased tissue.

2. A device according to claim 1, wherein said grid of holes has one or more of the following shapes:
    a rectangular pattern;
    a spherical pattern.

3. A device according to claim 1, wherein said mesh or plate comprises a plug per hole for connectivity with an electrode inserted in said hole, said plug being positioned around said hole.

4. A device according to claim 3, wherein said mesh or plate comprises:
    an electric cable connector for connectivity with said switch box; and
    electric wiring between each said plug and said electric cable connector.

5. A device according to claim 1, wherein said mesh or plate comprises a plug per hole for connectivity with an electrode-inserted in said hole, said plug being positioned near said hole.

6. A device according to claim 1, wherein said mesh or plate or an intermediate sterile plate comprises:
    a visual indicator per hole, said visual indicator being adapted to light up when an electrode is inserted in said hole, and said visual indicator further being operationally coupled to a visual indicator on said switch box, indicative for a plug on said switch box whereto said electrode has to be connected, said visual indicator on said mesh or plate and said visual indicator on said switch box enabling foolproof connectivity of said electrode to said switch box.

7. A device according to claim 6, wherein said visual indicator on said mesh or plate or intermediate sterile plate consists of a colour LED.

8. A device according to claim 1, wherein said mesh or plate constitutes a plate; said device further comprising a robot arm for positioning said plate.

9. A device according to claim 1, further comprising a robot arm for positioning said plurality of electrodes substantially parallel to each other.

10. A device according to claim 1, wherein each electrode of said plurality of electrodes has a sliding electrically insulating sheet for adapting said active tip length.

11. A device according to claim 10, wherein said electrically insulating sheet is coated with a coating that is visible through ultrasound.

12. A device according to claim 1, wherein one or more of said plurality of electrodes are partially shielded along their circumference for directing the RF field generated thereby near the border of said diseased tissue.

13. A device according to claim 12, wherein each partially shielded electrode has a shape that obstructs rotating said partially shielded electrode once inserted in said diseased tissue.

14. A device according to claim 1, wherein said plurality of electrodes have differing lengths.

15. A device according to claim 1, wherein said means for monitoring comprise:
- a ground plate; and
- means for measuring impedance between said ground plate and respectively each electrode of said plurality of electrodes.

16. A device according to claim 15, said device further comprising one or more of the following:
- means for transforming said impedance into information indicative for positions in said mesh or plate that are occupied;
- means for transforming said impedance into information indicative for the active tip length of each electrode; and
- means for transforming said impedance into information indicative for progress of said radio frequency ablation (RFA) process.

17. A device according to claim 1, wherein said means for monitoring comprise:
- means for measuring impedance between respective pairs of said plurality of electrodes.

18. A device according to claim 1, wherein said means for monitoring comprise:
- means for measuring impedance between a reference electrode and respectively each non-reference electrode of said plurality of electrodes.

19. A device according to claim 1, further comprising:
- means for logging parameters prior to and during said radio frequency ablation (RFA) process.

20. A device according to claim 1, further comprising:
- means for visualizing via a two dimensional (2D) representation and colours responsive to impedance measurements, the progress of said radio frequency ablation (RFA) process.

21. A device according to claim 1, further comprising:
- means for visualizing via a three dimensional (3D) representation taking into account the active tip lengths of said electrodes and colours responsive to impedance measurements, the progress of said radio frequency ablation (RFA) process.

22. A device according to claim 1, further comprising:
- an RF control interface for said switch box and/or a power unit.

* * * * *